US012740733B2

(12) United States Patent
Watts et al.

(10) Patent No.: US 12,740,733 B2
(45) Date of Patent: Sep. 22, 2026

(54) BLOOD SAMPLING DEVICE

(71) Applicant: Owen Mumford Limited, Woodstock (GB)

(72) Inventors: Matthew Watts, Woodstock (GB); Prem-Sagar Tank, Woodstock (GB); Oliver Hyde, Woodstock (GB); Clive Nicholls, Woodstock (GB)

(73) Assignee: Owen Mumford Limited, Woodstock (GB)

( * ) Notice: Subject to any disclaimer, the term of this patent is extended or adjusted under 35 U.S.C. 154(b) by 1467 days.

(21) Appl. No.: 17/279,340

(22) PCT Filed: Sep. 30, 2019

(86) PCT No.: PCT/EP2019/076487
§ 371 (c)(1),
(2) Date: Mar. 24, 2021

(87) PCT Pub. No.: WO2020/065099
PCT Pub. Date: Apr. 2, 2020

(65) Prior Publication Data

US 2022/0000402 A1 Jan. 6, 2022

(30) Foreign Application Priority Data

Sep. 28, 2018 (GB) ..................................... 1815946

(51) Int. Cl.
*A61B 5/15* (2006.01)
*A61B 5/151* (2006.01)

(52) U.S. Cl.
CPC .. *A61B 5/150412* (2013.01); *A61B 5/150022* (2013.01); *A61B 5/150549* (2013.01); *A61B 5/15144* (2013.01)

(58) Field of Classification Search
CPC ........ A61B 5/150412; A61B 5/150022; A61B 5/150549; A61B 5/15144;
(Continued)

(56) References Cited

U.S. PATENT DOCUMENTS 5,554,166 A 9/1996 Lang et al.
6,171,262 B1 * 1/2001 Bonaldo .......... A61B 5/150717 600/573

(Continued)

FOREIGN PATENT DOCUMENTS

CN 101987016 A 3/2011
CN 101466310 B 6/2011

(Continued)

OTHER PUBLICATIONS

International Search Report from corresponding International Application No. PCT/EP2019/076487, mailed Jun. 24, 2020, (7 pages).

(Continued)

*Primary Examiner* — Charles A Marmor, II
(74) *Attorney, Agent, or Firm* — Greenberg Traurig LLP

(57) ABSTRACT

A blood sampling device comprising a housing having an aperture in a forward end thereof and defining a passage having a longitudinal axis, a lancet comprising a lancet body supporting a lancet tip at a forward end thereof, said lancet being moveably mounted within said housing, an urging member configured to urge said lancet forwardly in said housing in use from a primed position in which said lancet tip is located within said passage to a lancing position in which said lancet tip projects through said aperture in said forward end of said housing and a removable safety cap configured to at least partially cover said lancet tip in said passage in an initial assembled configuration. The housing and said safety cap comprise cooperating abutment surfaces and cooperating stop surfaces, with the safety cap being
(Continued)

rotatable in a first direction relative to said passage from a first blocked position.

22 Claims, 14 Drawing Sheets

(58) Field of Classification Search
CPC .......... A61B 5/150916; A61B 5/15113; A61B 5/15117; A61B 5/1513; A61B 5/150442; A61B 5/150648; A61B 5/150885; A61B 5/15142
See application file for complete search history.

(56) References Cited

U.S. PATENT DOCUMENTS

2005/0143771 A1* 6/2005 Stout ................ A61B 5/150717 606/181
2008/0109025 A1* 5/2008 Yang .................. A61B 5/15117 606/182
2010/0042128 A1 2/2010 Curry et al.
2010/0042129 A1 2/2010 Curry
2011/0029006 A1 2/2011 Leong
2011/0144682 A1 6/2011 Hong
2012/0215246 A1* 8/2012 Hyoue ............. A61B 5/150259 606/182
2015/0142037 A1 5/2015 Nagao

FOREIGN PATENT DOCUMENTS

CN 103211602 B 11/2014
CN 204106725 U 1/2015
CN 106687040 A 6/2020
GB 2487188 A 7/2012
GB 2533620 A * 6/2016 ....... A61B 5/150022
WO 0078214 A1 12/2000
WO 02043591 A3 6/2002
WO 2009052710 A1 4/2009
WO 2015116698 A1 8/2015

OTHER PUBLICATIONS

Written Opinion of the International Searching Authority from corresponding International Application No. PCT/EP2019/076487, dated Jun. 24, 2020 (9 pages).
European Patent Office, Extended European Search Report for corresponding European Patent Application No. 23201538.8 dated Oct. 8, 2024 [11 pgs].

* cited by examiner

BLOOD SAMPLING DEVICE

CROSS-REFERENCE TO RELATED APPLICATIONS

The present application represents the United States National Stage of International Application No. PCT/EP2019/076487, filed Sep. 30, 2019, which relates to and claims priority to British Patent Application Serial No. GB 1815946.7, filed Sep. 28, 2018, both of which are incorporated herein by reference in their entirety.

The present invention relates to blood sampling devices of the type which employ a sharp tip or needle to obtain a small sample of blood for testing purposes. Particularly, though not necessarily, the invention relates to blood sampling devices suitable for disposal after a single use.

Blood sampling is an important part of daily routine for some people and in many cases may even be employed at home wherein the user may self-administer and/or may not be a trained medical professional. Accordingly, lancing devices are commonly used to provide a simple, reliable and repeatable method of collecting blood samples. Lancing devices are used to make a small incision at a sample site on the skin (typically for example a finger tip) to draw a sample of blood. Such devices may also be referred to as capillary blood sampling devices. Single use lancing devices (SULDs) are lancing devices that are intended to be disposed of after a single use. They are used for convenience and in order to reduce risk of infection and/or cross contamination between uses.

Known lancing devices (particularly SULDs), such as the Owen Mumford Unistik® range of devices, typically comprise a housing containing the lancet and a firing mechanism. The firing mechanism typically employs a spring or other biasing member which is arranged to urge the lancet forward in use when the device is fired (via a trigger mechanism) such that a skin piercing lancet tip extends beyond the end of the housing. When fired, the sharp tip of the lancet protrudes forwardly of the housing through the aperture with sufficient force to puncture the skin of the user such that blood is drawn for a sample. It will be appreciated that skin piercing lancet tip could be any suitable incision member, for example, a generally cylindrical needle, a sharp edge or a blade element. Typically the lancet tip will be metal and the lancet will also include an injection moulded plastic lancet body.

Some single use lancing devices require the lancet to be cocked or primed before being released, while others are assembled and sold in the cocked condition, ready to fire. In either case, it is desirable that single use devices are simple and relatively cheap such that they provide the convenience and hygiene of being able to be disposed of after a single use. It is known to provide such single use lancing devices with a needle cap which is removable prior to use of the device. However, in some instances, if a user does not follow the written and visual instructions, they may force the cap off in a way that causes the device to malfunction, e.g. accidentally trigger. It is therefore desirable to improve the safety of such devices to reduce the risk of malfunction and accidental triggering.

A common cause of accidental triggering in prior art devices is the 'cap pop indicator'. This is where upon initiation of removal of the safety cap, for example upon twisting of the safety cap, the link between the cap and the lancet body is partially severed, causing the cap to pop forwardly. This indicates to the user than the cap is ready to pull off even when the link between the safety cap and the lancet body is not fully severed. This suggests to the user that they can pull the cap forwardly to remove it from the device such that the lancet is ready to fire. If the link between the cap and the lancet body is not fully severed, and the user pulls the cap forwardly, this fires the lancet before the user has pressed the device against their skin.

Premature activation of the lancet is a serious problem as it means that a high proportion of devices fire before being pressed against the skin of the user and are wasted. Furthermore, this premature activation may also result in the user attempting to re-set the device and fire it again.

More experienced users may realise that this is an issue and so end up rotating the cap many times to ensure that the connection between the cap and the lancet body is severed fully before pulling. This can be time consuming and require additional effort, decreasing the convenience for the user.

Furthermore, known lancing devices are often relatively complicated to assemble due to a number of interconnected internal features of the device. For example, the firing mechanism on the lancing device is commonly a drive spring which must be fitted onto both the tail of the lancet and the rear end of the housing. This can increase the time and complexity of the device assembly, ultimately increasing costs.

It is also common for such prior art devices to malfunction after firing such that the drive spring remains extended and the lancet tip continues to project out of the forward aperture of the device. This can lead to needle stick injuries with potentially contaminated needles, putting anyone who comes into contact with the device before it is disposed of at risk.

It would therefore be desirable to provide a single use lancing device that overcomes at least some of the problems associated with prior art devices.

SUMMARY OF THE INVENTION

In accordance with a first aspect of the present invention, there is provided a blood sampling device comprising:

(i) a housing having an aperture in a forward end thereof and defining a passage having a longitudinal axis;

(ii) a lancet comprising a lancet body supporting a lancet tip at a forward end thereof, the lancet being moveably mounted within the housing;

(iii) an urging member configured to urge the lancet forwardly in the housing in use from a primed position in which the lancet tip is located within the passage to a lancing position in which the lancet tip projects through the aperture in the forward end of the housing;

(iv) a removable safety cap configured to at least partially cover the lancet tip in the passage in an initial assembled configuration;

wherein the housing and the safety cap comprise cooperating abutment surfaces and cooperating stop surfaces, wherein the safety cap is rotatable in a first direction relative to the passage from a first blocked position in which the cooperating abutment surfaces are in abutment alignment to prevent removal of the safety cap from the housing to a second passage position in which the cooperating abutment surfaces are not in abutment alignment such that the safety cap can be removed from the housing; and wherein the stop surfaces cooperate to limit further rotation of the safety cap relative to the passage in the first direction when the safety cap is in the second passage position.

This results in a blood sampling device in which premature activation of the lancet is prevented and the safety cap cannot be removed from the housing until it has been rotated by a predetermined degree. This requires an in-use deliberate twisting of the safety cap by the user. The stop surfaces limit relative rotational movement between the safety cap and the passage (and the housing). This stops users from rotating the cap many times, providing a more intuitive device with improved usability.

Preferably, the housing and the safety cap may each comprise second cooperating stop surfaces and the safety cap may be rotatable in a second direction relative to the passage from the first blocked position to a third passage position in which the abutment surfaces are not in abutment alignment such that the safety cap can be removed from the housing, wherein the second stop surfaces cooperate to prevent further rotation of the safety cap relative to the passage in the second direction when the safety cap is in the third passage position. This means that the user can rotate the safety cap in either direction with limited relative rotational movement between the safety cap and the housing/passage. This improves the usability of the device, meaning that left-handed and right-handed users may comfortably remove the safety cap.

Preferably, the blood sampling device is a single use lancing device. Preferably, the device is a side fire single use lancing device.

Preferably, movement of the safety cap from the first blocked position to the third passage position requires a predetermined degree of rotational movement in the second direction of between 30° and 70°, preferably between 30° and 60°, more preferably about 60°.

Preferably, movement of the safety cap from the first blocked position to the second passage position requires a predetermined degree of rotational movement in the first direction of between 30° and 70°, preferably between 30° and 60°, more preferably about 60°.

Alternatively, the predetermined degree of rotational movement in the first and/or second direction may be between 160° and 200°, preferably between 170° and 190°, more preferably about 180° or between 70° and 110°, preferably between 80° and 100°, preferably about 90°. As discussed above, providing a predetermined degree of rotation improves the usability of the device and prevents the user from unnecessarily expending time and effort by over-rotating the cap.

In some embodiments, the stop surfaces are formed by protrusions on the housing and the safety cap.

Preferably, the abutment surfaces cooperate to prevent forward movement of the safety cap during rotation of the safety cap from the first blocked position to the second passage position and/or the third passage position. This ensures that the cap does not pop forwardly until the cooperating stop surfaces engage one another and the safety cap is in the passage position for removal.

In certain embodiments, the cooperating abutment surfaces are formed by an abutment projection on one of the housing and the safety cap and a ledge on the other of the housing and the safety cap. Preferably, the cooperating abutment surfaces are formed by an abutment projection on the housing and a ledge on the safety cap. In this way, when the ledge is located rearwardly of the abutment projection, the safety cap cannot be pulled forwardly from the housing, preventing accidental actuation of the device.

In an advantageous embodiment, the safety cap comprises at least one longitudinal channel radially between the ledge and the or each stop surface through which the abutment projection can pass when the safety cap is in the second passage position or the third passage position such that the safety cap can be removed from the housing.

Preferably, the safety cap defines an arcuate slot therein configured to receive the abutment projection on the passage, the rearward surface of the slot forming the ledge on the safety cap. The provision of an arcuate slot not only provides a rearward ledge on the safety cap which prevents forward movement of the safety cap within the passage but also a forward ledge which prevents rearward movement of the safety cap within the passage which may affect the relative position of the components in the housing.

Preferably, the abutment projection on the housing forms one of the stop surfaces and at least one stop projection is provided in the arcuate slot of the safety cap to form the or each other of the stop surfaces. The safety cap may define a substantially longitudinal channel therein immediately radially adjacent the or each stop projection and connected to the arcuate slot, wherein the substantially longitudinal channel is configured to enable passage of the abutment projection when the safety cap is in the second position such that the safety cap can be removed from the housing. Thus, a defined passage is provided for the abutment projection for movement from the initial assembled position to removal of the safety cap from the housing. This means that there is a defined and reproducible movement for removal of the safety cap that the user can be confident will prime the device without premature activation of the lancet for each single use lancing device that they use.

In certain embodiments, one of the passage and the safety cap comprises two diametrically opposed stop surfaces. The first of the diametrically opposed stop surfaces may define the rotational position of the safety cap relative to the passage in the second passage position and the second of the diametrically opposed stop surfaces may define the rotational position of the safety cap relative to the passage in the first blocked position. More specifically, the first of the diametrically opposed stop surfaces may limit or prevent rotation of the safety cap relative to the passage in the first direction and the second of the diametrically opposed stop surfaces may limit or prevent rotation of the safety cap relative to the passage in a second opposite direction.

Preferably, the or each stop surface is formed by a protrusion on the passage and/or the safety cap. Preferably, the safety cap comprises a protrusion and the forward surface of the protrusion forms the ledge on the safety cap.

Optionally, the stop surface of either the housing and/or the safety cap comprises an angled portion. The stop surfaces may be configured to act as a cam. In this configuration the removal of the cap is facilitated as it reduces the amount of direct pulling on the cap by the user as the force required to separate the cap from the lancet is applied during rotation of the cap. Further, by facilitating removal of the cap during rotation the likelihood of premature firing due to pulling the cap out of alignment with the lancet is reduced.

Preferably, the housing comprises a fixed detent for holdingly engaging the lancet in the rearward primed position i.e. for engaging/abutting a surface of the lancet to prevent forward movement thereof from the rearward primed position to the forward lancing position. By using a fixed detent on the housing to retain the lancet in a rearward primed position, a more stable and secure latching of the lancet may be provided in comparison to prior art devices in which a trigger member (which will generally be moveably mounted to the housing) is required to retain the lancet. This can be particularly advantageous in resisting any unintentional movement/release of the lancet during cap removal.

Advantageously, the lancet may comprise a boss configured to engage the fixed detent such that the lancet is holdingly engaged in the primed position.

Preferably, the device further comprises a trigger moveable from a rest position to a fire position to release the lancet for forward movement, wherein the trigger deflects at least a portion of the lancet body in a direction generally transverse to the longitudinal axis of the housing such that the lancet body may move forwardly past the detent.

Movement of the trigger from the rest position to the fire position may be a generally transverse movement relative to the longitudinal axis of the housing. The device may be a side-fire single use lancing device. Movement of the trigger from the rest position to the fire position may push a portion of the trigger into the passage of the housing. Prior to removal the safety cap may support the lancet body within the device such that it cannot be deflected transversely past the detent.

In a preferred embodiment, in the initial assembled configuration, the safety cap holds the lancet in a rearward pre-primed position such that it does not engage or abut the detent, wherein upon removal of the safety cap, the lancet can move forwardly from the pre-primed position into the primed position in which the detent holdingly engages the lancet i.e. the detent engages/abuts a surface of the lancet to prevent forward movement thereof from the rearward primed position to the forward lancing position. This can provide the user with an indication of when the device is primed and ready to fire.

Preferably, the housing comprises a stop feature configured to prevent the lancet from being deflected transversely in the passage when the lancet is in the pre-primed position. In one embodiment, the housing comprises a stop feature configured to prevent the lancet from being deflected transversely past the abutment until the lancet moves forwardly from the pre-primed position into the primed position. This further prevents premature activation of the device. The stop feature may comprise a protrusion on the housing projecting into the passage. The stop feature may comprise a substantially longitudinal rib on the housing projecting into the passage. The stop feature may be diametrically opposite the trigger member. This can prevent transverse movement of the lancet body in the passage by providing a portion of the passage having a reduced diameter and can in turn prevent depression of the trigger member. The stop feature is a physical abutment preventing transverse movement of the lancet in the passage.

Preferably, the stop feature may comprise a leg projecting from the rear of the housing. Friction between the stop feature and the lancet body may prevent forward movement of the lancet body from the pre-primed position to the primed position when the trigger is depressed. This means that even if a user were to inadvertently depress the trigger when removing the safety cap, the lancet would not move forwardly in the housing and accidentally fire due to the friction between the base of the trigger and the upper surface of the lancet body and the friction between the lower surface of the lancet body and the stop feature. Pressure would need to be removed from the trigger to enable the lancet body to move forwardly, at which point the lancet would move upwardly in the housing and forwardly to the primed position in which it is held by the detent in the housing.

Advantageously, the housing may be formed of a forward housing body and a rearward housing end cap, the forward housing body comprising a longitudinal slot and the rearward housing end cap comprising a longitudinal trigger configured to fit in the longitudinal slot when the device is assembled. This arrangement is beneficial as it simplifies assembly of the device. Each of the internal components of the device may be assembled along the longitudinal axis of the device in the housing body and then the housing end cap may fitted thereon. The forward housing body and the rearward housing end cap may comprise a snap fit arrangement for joining them together. Preferably, the forward housing body and the rearward housing end cap are joined together with a snap fit arrangement. Preferably, they can be snap fitted together during assembly. The stop feature may comprise a leg (as discussed above) projecting from the end cap (i.e. the trigger and the stop feature are both formed on the end cap).

In a preferred embodiment, the housing may comprise an externally visible indicator of movement of the lancet body from the pre-primed to the primed position. The housing may comprise (i.e. define) an opening or a window configured to enable the user to see when the lancet body has moved from the pre-primed to the primed position. This provides the user with a visual indicator of when the device is primed and ready to fire. This again reduces the chance of premature activation of the device.

Preferably, the housing comprises a trigger member and an opening defined between the forward end of the trigger member and the housing configured to enable the user to see when the lancet body has moved from the pre-primed to the primed position. In such embodiments, the device may be a side fire single use lancing device. Optionally, the lancet body may not be visible in the opening or window after firing. This provides the user with a visual indicator of when the device has been used and should be disposed of and reduces the chance of the user trying to re-use the.

Preferably, the safety cap is frangibly connected to the lancet body. Preferably, rotation of the safety cap from the first position to the second position is sufficient to sever the frangible connection between the safety cap and the lancet body. Thus, the user can twist the safety cap from the first position in which the safety cap cannot be removed from the housing to the second position in which the safety cap can be removed from the housing and be confident that the safety cap is no longer connected to the lancet body in this second position. Therefore, the lancet body will not be pulled forward with the safety cap which could otherwise cause premature activation of the device.

In certain embodiments, at least one of the safety cap and the lancet body comprises an anti-deflection feature configured to interact with the other of the lancet body and the safety cap to restrict the degree to which the safety cap and the lancet body can be misaligned relative to the longitudinal axis in the initial assembled configuration. The longitudinal axis may refer to the longitudinal axis of the housing. Misalignment may occur without this feature if the cap is angularly moved outside the housing because the lancet is constrained at both its front end and its rear end whilst the cap is in place. In embodiments where the housing comprises a fixed detent for holdingly engaging (i.e. physically retaining) the lancet in the rearward primed position, the misalignment may be constrained to be below a certain distance such that the lancet is not able to move far enough in a direction transverse to the longitudinal axis of the device to become disengaged from the detent on the housing. Therefore, this prevents the device from firing before and during removal of the safety cap (i.e. the cap must be removed before the device can be fired).

In certain embodiments, the safety cap and the lancet body comprise adjacent surfaces frangibly connected by a narrowing therebetween and the anti-deflection feature is a protrusion on at least one of the adjacent surfaces configured to interact with the other of the adjacent surfaces to prevent angular movement therebetween. One or both of the adjacent surfaces may be an angled surface relative to the longitudinal axis, for example, the surface may be a conical shape, to provide the narrowing therebetween. Prevention of misalignment avoids a situation in which the plastic connection between the lancet cap and lancet body is broken, which would compromise the sterility of the lancet, without the user being aware that the sterility had been compromised.

In certain embodiments, the device further comprises means for preventing rearward movement of the lancet body from the lancing position to the primed position. The means for preventing rearward movement of the lancet body from the lancing position to the primed position may comprise a polygonal wall extending from the rearward wall of the housing into the passage and being shaped and configured to deflect the lancet body in the passage to prevent re-priming of the lancet body. Prevention of re-priming is beneficial as it stops the device from being able to re-fire once it has been used. This therefore prevents contaminated needles from being re-used, improving the safety of the device.

Preferably, the device further comprises a return spring configured to urge the lancet into a safe position in which the lancet tip is located in the housing after firing. This ensures that the lancet does not stay in the lancing position with the lancet tip outside of the housing after use. Thus this prevents accidental needlestick injuries and improves the safety of the device.

Preferably, the return spring is freely mounted in the housing (i.e. it is not interconnected with any other component). Preferably, the drive spring is freely mounted in the housing (i.e. it is not interconnected with any other component). This reduced the number of interconnected parts, simplifying the assembly of the device. This also means that there is no need to mould features into the lancet which enable a reliable connection between the lancet and the drive spring (e.g. between the housing, the drive spring, and the lancet body), simplifying manufacture and that there is no need to have a means for automatically connecting the return spring to the lancet body.

Preferably, the lancet body and the housing comprise cooperating features configured to constrain the lancet body against rotation relative to the housing. The lancet body may comprise a pair of wings and the passage may comprise a pair of corresponding tracks configured to guide the lancet body within the passage.

Preferably, the passage comprises a shoulder configured to limit forward movement of the lancet body in the housing when the lancet body is in the lancing position.

In accordance with a second aspect of the present invention, there is provided a blood sampling device comprising:

- (i) a housing having an aperture in a forward end thereof and defining a passage having a longitudinal axis;
- (ii) a lancet comprising a lancet body supporting a lancet tip at a forward end thereof, the lancet being moveably mounted within the housing;
- (iii) an urging member configured to urge the lancet forwardly in the housing in use from a primed position in which the lancet tip is located within the passage to a lancing position in which the lancet tip projects through the aperture in the forward end of the housing;
- (iv) a removable safety cap configured to at least partially cover the lancet tip in an initial assembled configuration;

wherein the safety cap and the lancet body comprise adjacent surfaces frangibly connected by a narrowing therebetween, at least one of the adjacent surfaces comprising a protrusion thereon configured to interact with the other of the adjacent surfaces to restrict relative angular movement between the lancet body and the safety cap away from the longitudinal axis of the housing.

Prevention of misalignment avoids a situation in which the plastic connection between the lancet cap and lancet body is broken, which would compromise the sterility of the lancet, without the user being aware that the sterility had been compromised.

In certain embodiments, at least one of the safety cap and the lancet body comprises an anti-deflection feature configured to interact with the other of the lancet body and the safety cap to restrict the degree to which the safety cap and the lancet body can be misaligned relative to the longitudinal axis in the initial assembled configuration.

One or both of the adjacent surfaces may be an angled surface relative to the longitudinal axis, for example, the surface may be a conical shape, to provide the narrowing therebetween. Misalignment may occur without this feature if the cap is angularly moved outside the housing because the lancet is constrained at both its front end and its rear end whilst the cap is in place.

In embodiments where the housing comprises a fixed detent for holdingly engaging (i.e. physically retaining) the lancet in the rearward primed position, the misalignment may be constrained to be below a certain distance such that the lancet is not able to move far enough in a direction transverse to the longitudinal axis of the device to become disengaged from the detent on the housing. Therefore, this prevents the device from firing before and during removal of the safety cap (i.e. the cap must be removed before the device can be fired).

Preferably, the protrusion is provided on the safety cap, more preferably on a surface of the safety cap adjacent the trigger on the housing.

In accordance with a third aspect of the present invention, there is provided a blood sampling device comprising:

- (i) a lancet comprising a lancet body and a lancet tip at a forward end thereof;
- (ii) an urging member;
- (iii) a housing configured to house the lancet and the urging member, wherein the housing comprises:

- (a) a first housing member comprising a longitudinal receptacle having a forward end defining an aperture through which the lancet tip projects in use and a substantially open rearward end; and
- (b) a second housing member comprising a cap member for closing the rearward end of the first housing member, wherein the first housing member defines a longitudinal slot therein extending forwardly from the rearward end thereof and the second housing member comprises a longitudinal trigger member configured to fit in the slot, the trigger member being moveable from a rest position to a fire position to actuate the lancet such that the urging member urges the lancet forwardly in the housing in use, wherein the first and second housing members comprise cooperating engagement features for securing the second housing member to the first housing member.

There may be provided a blood sampling device comprising: a housing having an aperture in a forward end thereof and defining a passage having a longitudinal axis; a lancet comprising a lancet body supporting a lancet tip at a forward end thereof, said lancet being moveably mounted within said housing an urging member configured to urge said lancet forwardly in said housing in use from a primed position in which said lancet tip is located within said passage to a lancing position in which said lancet tip projects through said aperture in said forward end of said housing and means for preventing rearward movement of said lancet body from said lancing position to said primed position. Preventing rearward movement of the lancet body means that the device cannot be re-primed for re-use.

The means for preventing rearward movement of said lancet body may comprise a rearward projection from the lancet body and a leg projecting from the rear of said housing. The rearward projection and said leg may be in alignment in the lancing position. The rearward projection and/or said leg comprise an angled face such that when the lancet is moved rearwardly and the rearward projection and leg come into contact because they are aligned the rearward projection is diverted away from the primed position. Preferably the rearward projection is diverted underneath the leg although the skilled person would understand that a sideways diversion or diversion in any other direction that the direction placing the lancet in the primed position may be sufficient.

In the initial assembled configuration, the lancet may held in a rearward pre-primed position, the leg being configured to prevent the lancet from being deflected transversely past the detent until the lancet moves forwardly from the pre-primed position into the primed position.

The means for preventing rearward movement may further comprise one or more ribs projecting from the rear of said housing.

There may be provided a blood sampling device comprising: a housing having an aperture in a forward end thereof and defining a passage having a longitudinal axis, a lancet comprising a lancet body supporting a lancet tip at a forward end thereof, said lancet being moveably mounted within said housing, an urging member configured to urge said lancet forwardly in said housing in use from a primed position in which said lancet tip is located within said passage to a lancing position in which said lancet tip projects through said aperture in said forward end of said housing; and wherein said lancet body comprises at least one outward projection and said passageway is provided with at least one track to support said outward projection.

The at least one track may comprise a surface extending longitudinally at least a portion of the length of the passage.

The housing may comprise a trigger member and the track may comprise two portions, the rearward portion being closer than the forward to the side of the housing in which the trigger member is disposed. This allows the track to support the outward projection when the device is in a pre-primed position such that pressure on the lancet by the trigger does not result in firing of the device.

The housing may be formed of a forward housing body (20) and a rearward housing end cap (30), the rearward portion of the track being disposed on the rearward housing end cap and the forward portion of the track being disposed on the forward housing body (20).

In the initial assembled configuration, said safety cap may hold the lancet in a rearward pre-primed position on the rearward portion of the track, wherein upon removal of said safety cap, said lancet can move forwardly off the rearward portion of the track. Removal of said safety cap, may cause said lancet to move forwardly onto the forward portion of the track.

The lancet may move forwardly onto the forward portion of the track when said lancet moves to said lancing position.

The outward projection comprises an arcuate surface at the forward end thereof. This smooths the movement of the lancet onto track. This has the advantage, for example, that it reduces the likelihood of a rearward force being exerted on the lancet on contact between the outward projection and the track.

There may be provided a blood sampling device comprising: a housing having an aperture in a forward end thereof and defining a passage having a longitudinal axis, a lancet comprising a lancet body supporting a lancet tip at a forward end thereof, said lancet being moveably mounted within said housing, an urging member configured to urge said lancet forwardly in said housing in use from a primed position in which said lancet tip is located within said passage to a lancing position in which said lancet tip projects through said aperture in said forward end of said housing; wherein the housing comprises a trigger member and, in the initial assembled configuration, said lancet is held in a rearward pre-primed position where the trigger member cannot release the urging member. This reduces the likelihood of accidental activation of the device.

In the initial assembled configuration, said safety cap may hold said lancet in the rearward pre-primed position.

The housing may comprise a fixed detent for holdingly engaging the lancet in the primed position. The lancet may comprise a boss configured to engage the fixed detent such that the lancet is holdingly engaged the in the primed position.

The trigger member may be moveable from a rest position to a fire position to release the lancet for forward movement, wherein the trigger deflects at least a portion of the lancet body in a direction generally transverse to the longitudinal axis such that the lancet body may move forwardly past the detent. Movement of the trigger from the rest position to the fire position may be in a generally transverse movement relative to the longitudinal axis.

The blood sampling device may include a safety cap and, prior to removal, said safety cap supports said lancet body in the pre-primed position such that it cannot be deflected transversely past said detent.

The housing may include a stop feature configured to prevent the lancet from being deflected transversely past the detent until the lancet moves forwardly from the pre-primed position into the primed position. The stop feature may be a leg projecting from the rear of said housing. Friction between said stop feature and said lancet body may prevents forward movement of the lancet body from said pre-primed position to said primed position when said trigger is depressed.

The stop feature may include a projection from the boss which comprises an abutment surface, the abutment surface being configured to engage with the housing when the lancet is in the pre-primed position. The stop feature may additionally include an abutment surface of a housing configured to engage with the abutment surface of the boss when the lancet is in the pre-primed position and not engage with the abutment surface of the boss when the lancet is in the primed position.

The stop feature comprises at least one outward projection on the lancet body and a track to support said outward projection in the passageway wherein at least a portion of the track is disposed such that, when the device is in the pre-priming position the outward projection and the at least a portion of the track are in contact such that the trigger member cannot release the urging member.

The housing comprises an externally visible indicator of movement of said lancet body from the pre-primed position to the primed position, for example, an opening or a window (18) configured to enable the user to see when said lancet body has moved from the pre-primed position to the primed position. The housing may comprise a trigger member and an opening (18) between a forward end of said trigger member and said housing configured to enable the user to see when the lancet body has moved from the pre-primed position to the primed position. The lancet body may not be visible in said opening or window (18) after firing.

This simplifies assembly of the device as all internal components of the device can be assembled along the longitudinal axis of the device inside the first housing member.

Preferably, the first housing member comprises a fixed detent for holdingly engaging the lancet in the rearward primed position i.e. for engaging/abutting a surface of the lancet to prevent forward movement thereof from the rearward primed position to the forward lancing position.

Preferably, movement of the trigger member from the rest position to the fire position deflects at least a portion of the lancet body in a direction generally transverse to the longitudinal axis of the housing such that the lancet body may move forwardly past the detent.

In certain embodiments, the cooperating engagement features are cooperating snap fit engagement features. The first housing member may comprise a fixed abutment surface for holdingly engaging (i.e. physically retaining) the lancet body in a rearward primed position. This can prevent accidental actuation of the device. Movement of the trigger member from a rest position to a fire position may deflect at least a portion of the lancet body in a direction generally transverse to the longitudinal axis such that the lancet body may move forwardly past the fixed abutment surface. Movement of the trigger from the rest position to the fire position may be a generally transverse movement relative to the longitudinal axis.

Unless the context dictates otherwise, the optional features of the different aspects of the present invention apply equally to one another.

These and other aspects of the present invention will be apparent from the following specific description, in which embodiments of the present invention are described, by way of examples only, and with reference to the accompanying drawings, in which.

Figure 1:
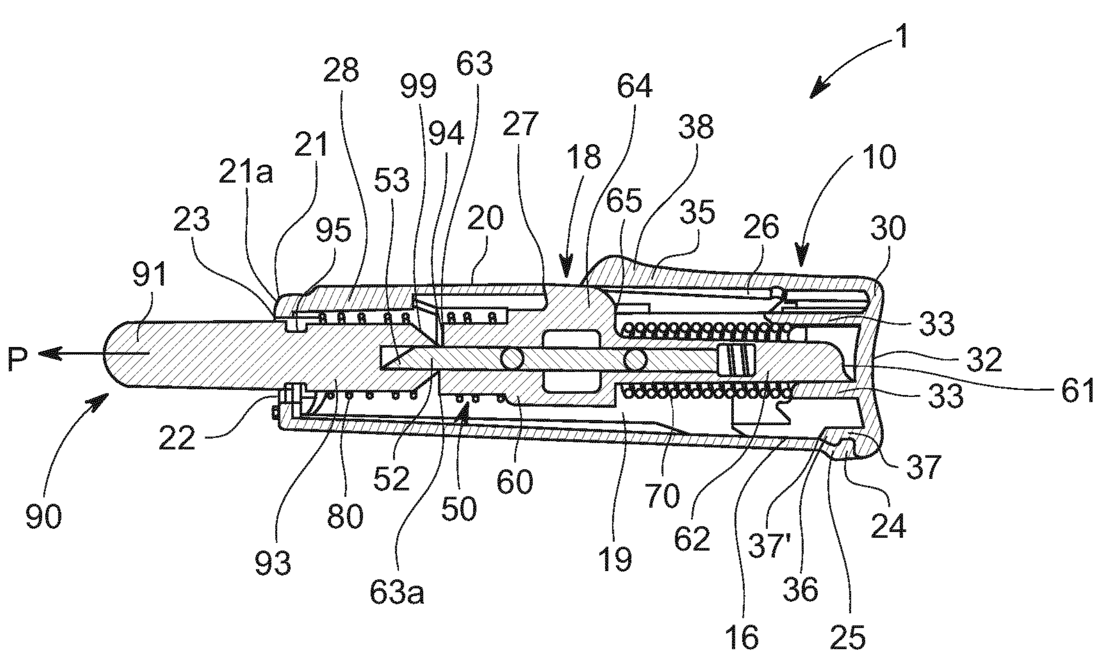
FIG. 1 is a schematic longitudinal cross-sectional side view of a blood sampling device according to a first exemplary embodiment of the present invention in an initial assembled configuration.

A list of the reference signs used herein is given at the end of the specific embodiments. Repeat use of reference symbols in the present specification and drawings is intended to represent the same or analogous features or elements.

Directional descriptors as used in the following description of the preferred embodiments of the present invention, such as “upper”, “lower”, “top”, “bottom”, “front”, “rear”, etc. relate to the invention when in the preferred orientation. However, it will be clear to the skilled person that the device may be in any orientation and therefore the directional descriptors would be changed accordingly.

“Front” and “forward end” as used herein refers to the end of the lancing device (or components thereof) which, in use, are closest to the sample site end of the device (i.e. the end which is pointed at the skin). “Rear” and “rearward end” as used herein refers to the end of the lancing device (or components thereof) which, in use, are furthest from the sample end of the device (i.e. the end which is pointed away from the skin). "Forward" and "rearward" likewise refer to the directions orientated towards the front and rear of the device.

The terms "axial", "radial" and "circumferential" are used herein to conveniently refer to the general directions relative to the longitudinal direction of the device (or components thereof). The skilled person will, however, appreciated that these terms are not intended to be narrowly interpreted (and for example, the device may have a non-circular and/or irregular form). Typically, regardless of the specific and aesthetic design of the lancing device the device will be generally elongate and have a longitudinal axis that is generally aligned with the lancing needle and the forward/rearward direction of travel of the lancet in use, as such, the longitudinal axis of the device will substantially coincide with (or be parallel to) the axial direction of the lancet.

Embodiment 1

Referring to FIGS. 1 to 6, a blood sampling device 1 according to a first exemplary embodiment of the present invention includes a plastic housing 10 containing a lancet 50, a drive spring 70 and a return spring 80. Both the drive spring 70 and the return spring 80 are compression springs.

The housing 10 is formed of two main components; a first housing member which is a housing body 20 and a second housing member which is a housing end cap 30. The housing body 20 is an injection moulded plastic component forming a longitudinal cylindrical receptacle having at its forward end 21 a planar front face 21*a* defining a circular aperture 22 therein. Projecting from the front face 21*a* in an annular array around the aperture 22 are a plurality of projections 23 which are designed to stimulate the skin to 'confuse' the nerve endings and alleviate the perceived pain experienced when the lancet tip 53 penetrates the skin to make an incision. The rear end 24 of the housing body 20 is open with an oval-shaped cross-section to receive the internal components of the blood sampling device 1 during assembly. Spaced forwardly from the circumferential edge of the rear end 24 and on an internal surface 16 of the housing body 20 is a circumferential notch 25. Extending forwardly from the open rear end 24 and forming a gap in the circumferential notch 25 is an elongate cut-out 26 having a substantially rectangular shape. The forwardmost edge of the cut-out 26 is curved and forms a detent 27.

The internal surface 16 of the housing body 20 defines a passage 19 having a pair of diametrically opposed tracks 14 for guiding the lancet 50 in use. The internal surface 16 of the housing body 20 comprises a first longitudinal rib 28 projecting into the passage 19 and extending rearwardly from the front 21 of the housing body 20. The internal surface 16 of the housing body 20 also comprises a radial abutment projection (tooth) 29 located just rear of the aperture 22 which projects into the bore of the aperture 22 to provide a narrowed portion thereof.

The housing end cap 30 is an injection moulded plastic component comprising a base 32 having a curved central indentation. The housing end cap 30 has a circumferential wall 37 extending perpendicularly to the base 32 around the periphery of the base 32 which has a longitudinal gap (not shown) therein. An elongate trigger member 35 having a textured (ribbed) outer surface 38 extends substantially perpendicularly from the base 32, passing through the gap in the wall 37 of the end cap 30. An outwardly protruding engagement rib 36 extends around the circumferential forward edge 37' of the wall 37 of the housing end cap 30. The engagement rib 36 is shaped and dimensioned to form a snap fit in the notch 25 of the housing body 20. As the wall 37 fits flush to the internal surface 16 of the housing body 20 and the engagement rib 36 forms a snap fit with the notch 25 of the housing body 20, they assist in guiding the housing end cap 30 into the open end 24 of the housing body 20 during assembly and stabilising the housing end cap 30 in the housing body 20 after assembly. An oblong walled portion 33 projects substantially perpendicularly from the base 32 and is spaced radially inwardly from the circumferential edge thereof to define a recess within which the rear end of the lancet tail 62 sits in the initial assembled configuration.

The lancet 50 comprises a lancet body 60 moulded around a needle 52, the sharp tip 53 of the needle 52 projecting from a forward surface 63*a* of the lancet body 60. The lancet body 60 comprises a pair of diametrically opposed radial wings 66 which project horizontally in the device at an angle of roughly 90° from the immediately adjacent surfaces of the lancet body 60. The radial wings 66 are configured to interact with the diametrically opposed tracks (14) on the passage 19 of the housing body 20 to guide the lancet 50 during use. The lancet body 60 also comprises a boss 64 projecting from the upper surface thereof. The rear surface 65 of the lancet body 60 has an elongate rearwardly extending tail 62 projecting therefrom.

Figure 6:
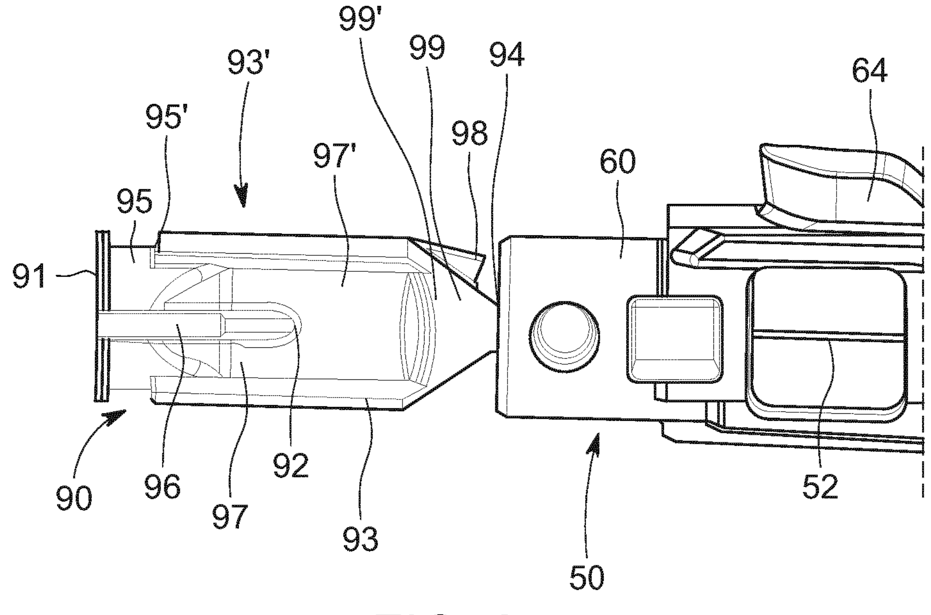
FIG. 6 is a schematic side view of a lancet and safety cap of a blood sampling device according to an exemplary embodiment of the present invention in an initial assembled configuration.

Referring to FIG. 6, an elongate safety cap 90 is integrally moulded with the forward surface 63*a* of the lancet body 60 such that the lancet needle 52 is initially concealed within the safety cap 90 to maintain the sterility of the needle 52 prior to use. The safety cap 90 has a graspable portion 91 at a first forward end thereof which is connected to a stem 93 at a second rearward end thereof. The stem 93 of the safety cap 90 comprises a conical portion 99 which narrows towards a connection point 94 which connects the safety cap 90 to the forward surface 63*a* of the lancet body 60 such that the two components are frangibly connected. The conical portion 99 focusses the torsion when the safety cap 90 is twisted relative to the lancet 50 on the connection point 94, making it easier to break the frangible connection 94 so that the safety cap 90 can be removed. Provided on the conical portion 99 is an integrally formed protrusion 98. The protrusion 98 projects toward the forward surface 63*a* of the lancet body 60, decreasing the relative distance therebetween such that relative angular movement between the safety cap 90 and the lancet 50 is limited.

Figure 6A:
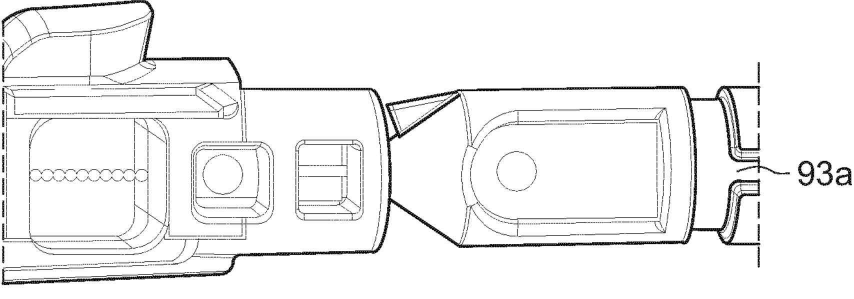
FIG. 6A is a schematic side view of FIG. 6, rotated through 180 degrees to show the reverse face.

The safety cap 90 comprises an annular slot 95 which is shaped and dimensioned to receive the abutment projection (tooth) 29 on the passage 19 of the housing body 20 when the device 1 is in an initial assembled configuration. The annular slot 95 is narrower than the immediately rearward portion of the stem 93 of the safety cap 90 such that a ledge 95' is formed on the stem 93 of the safety cap 90. The annular slot 95 has a single longitudinal stop 96, spanning the width of the annular slot 95 and extending rearwardly along the external surface 93' of the stem 93. The stop 96 is spaced by about 120-160° from the abutment projection (tooth) 29. The stop 96 is spaced from each other by about 120-160° on a first side of the stem 93 of the lancet cap 90 to form a first arcuate segment 95*a* of the annular slot 95. As shown in FIG. 6A, on the opposing side of the stem 93 of the lancet cap 90 there is a slot 93*a* which allows the lancet to assemble in to the body by allowing the abutment projection (tooth) 29 to pass through it. The skilled person would be aware that this spacing could be modified depending on the desired degree of rotation of the safety cap 90 prior to removal of the safety cap 90. Extending rearwardly from the annular slot 95 on either side of each stop 96 is a pair of elongate longitudinal channels 97. Each pair of longitudinal channels 97 is connected to the annular slot 95 and merge at the rearwardmost end 92 of the stop 97 to form a single channel 97' extending rearwardly to a midpoint 99' in the in the conical narrowing 99 of the stem 93.

During assembly, the housing body 20 is oriented with the rearward non-pricking end 24 facing upwards.

Firstly, the return spring 80 is dropped into the housing body 20 via the rearward end 24 of the housing body 20. As the return spring 80 is a compression spring, the rotational orientation of the return spring 80 in the housing body 20 does not matter, i.e. the return spring 80 can be located in the housing body 20 in any rotational orientation. The return spring 80 is not physically inter-connected with any components in the housing body 20.

Secondly, the safety cap 90 and frangibly connected lancet 50 are dropped into the housing body 20 via the rearward end 24 of the housing body 20. The graspable portion 91 of the safety cap 90 is dimensioned such that it can pass through the circular aperture 22 in the front face **21*a* of the housing body 20 such that it is located outside of the housing 10 in the initial assembled configuration. The lancet 50 is rotationally aligned so that the boss 64 on the lancet body 60 is located within elongate cut-out 24 in the housing body 20 with the forward surface of the boss 64 contacting the detent 27. In this rotational orientation, the safety cap 90 is in a blocked position, wherein the rearward ledge 95' of the annular slot 95 of the safety cap 90 abuts the abutment projection (tooth) 29 which projects into the bore of the passage 19 of the housing body 20. This prevents forward movement of the safety cap 90 and frangibly connected lancet 50 in the housing. Therefore, the stem 93 of the safety cap is located in the passage 19** in the initial assembled configuration.

Figure 7A:
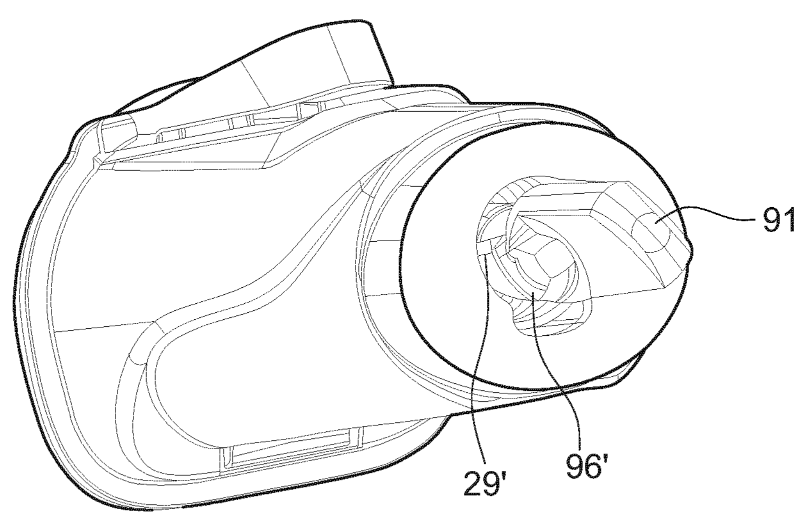
FIGS. 7A and 7B illustrate and alternative implementation of the safety cap and housing.
Figure 7B:
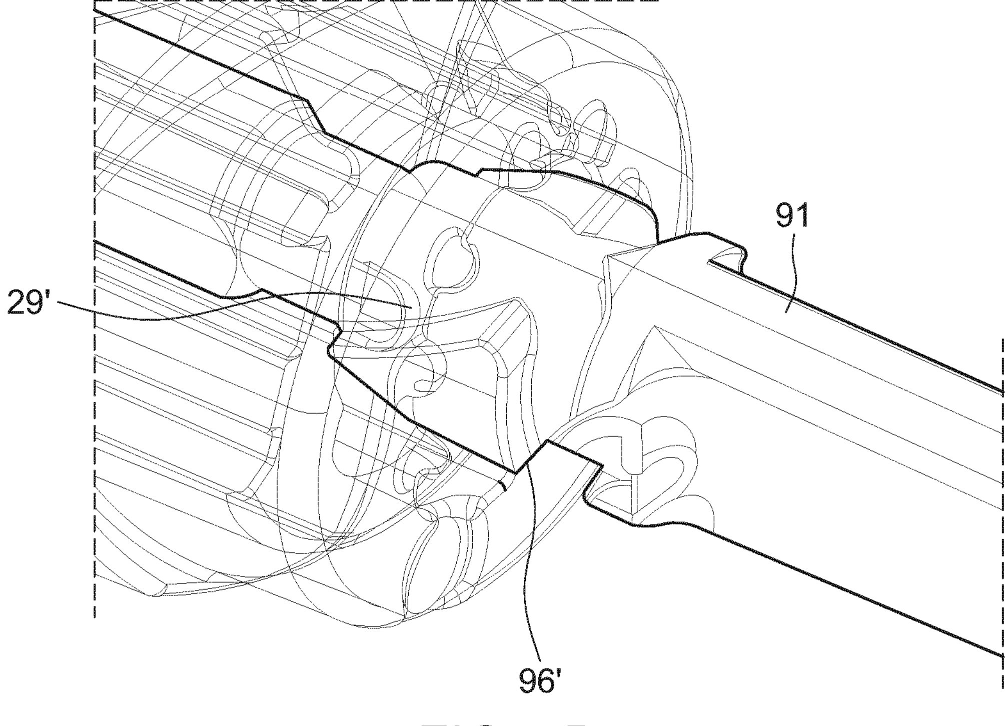

The stop 96 may have a longitudinal surface as shown and described with reference to FIG. 6. Alternatively, the stop 96 may be provided with an angled or curved surface as illustrated in FIG. 7. For example, the stop 96' may have the form of an inverted triangle. By having an angled or curved surface the cap receives an outward force away from the lancet body 60 to assist the removal of the cap 91 from the lancet body 60. Optionally, the tooth 29' may be provided with a curved or angled surface to further assist removal of the cap 91 from the lancet body 60. In a further arrangement the tooth 29' and stop 96' may both be provided with angled and/or curved surfaces in order for form a cam arrangement to assist removal of the cap 91 from the lancet body 60.

Thirdly, the drive spring 70 is dropped into the housing body 20 via the rearward end 24 of the housing body 20 such that it surrounds the rearward tail 62 of the lancet body 60. As the drive spring 70 is a compression spring, the rotational orientation of the drive spring 70 in the housing body 20 does not matter, i.e. the drive spring 70 can be located in the housing body 20 in any rotational orientation. The drive spring 70 is not physically inter-connected with any components in the housing body 20.

Finally, the housing end cap 30 is rotationally aligned with the housing body 20 such that the trigger member 35 is aligned with the elongate cut-out 26 in the housing body 20 (i.e. located radially above the elongate cut-out 26 and the boss 64 on the lancet body 60). The end cap 30 is placed over the lancet tail 62 such that the rear end of the lancet tail 62 is located in the recess formed by the oblong walled portion 33 on the base 32 of the end cap 30. As such, the housing end cap 30 interacts with the lancet 50 before the housing body 20, ensuring that end cap 30 assembles in the correct position in relation to the lancet 50.

The housing end cap 30 is then pushed into the rear end 24 of the housing body 20 such that the engagement rib 36 of the end cap 30 forms a snap fit in the notch 25 of the housing body 20. There is a gap or window 18 between the forwardmost edge of the trigger member 35 and the detent 27 such that the user can see the boss 64 on the lancet body 60 resting against the detent 27 on the housing body 20.

Referring now to FIG. 1, in the initial assembled configuration, if the user tries to pull the graspable portion 91 of the safety cap 90 in the pricking direction P, neither the safety cap 90 nor the lancet body 50 will move forwardly in the pricking direction P as the safety cap 90 is in a blocked position. More specifically, the abutment projection 29 on the housing body 20 is located in the annular slot 95 on the safety cap 90. As the annular slot 95 is narrower than the immediately rearward portion of the stem 93 of the safety cap 90, a ledge 95' is formed on the stem 93 of the safety cap 90. Abutment of the abutment projection 29 against this ledge 95' (see FIG. 6) prevents forward movement of the lancet cap 90 relative to the housing body 20 and thus removal of the safety cap 90 from the housing body 20. This prevents the user from pulling the safety cap 90 out of the housing body 20 before the frangible connection 94 between the safety cap 90 and the lancet body 20 is severed, preventing premature activation of the device. This also prevents the lancet 50 and safety cap 90 from moving forwardly relative to the housing body 20 if the trigger member 35 is depressed, preventing accidental actuation of the blood sampling device 1 in the initial assembled configuration.

The safety cap 90 may be removed by holding the graspable portion 91 and twisting it relative to the housing body 20 about the direction of pricking P (i.e. about the longitudinal axis of the device 1). The lancet 50 is constrained against rotation relative to the housing body 20 by the location of the boss 64 on the lancet body 60 within the elongate cut-out 24 in the housing body 20. As such, twisting the safety cap 90 relative to the housing body 20 about the direction of pricking P also rotates the safety cap 90 relative to the lancet 50. Rotation of the safety cap 90 relative to the housing body 20 is enabled as the abutment projection 29 is located in the annular slot 95 of the safety cap 90. However, rotation of the safety cap 90 relative to the housing body 20 is only enabled to a certain predetermined degree. When the abutment projection 29 contacts one of the stops 96 in the annular slot 95 further rotational movement of the safety cap 90 relative to the housing 20 in this direction is prevented. The predetermined degree of rotation is set by the relative positions of the abutment projection 29 on the housing body 20 and the stops 96 in the annular slot 95 in the initial assembled configuration. In this case, the safety cap 90 can be rotated by up to 160° in either direction from the initial assembled configuration in which the safety cap 90 is in a blocked position until the abutment projection 29 contacts a stop 96. This prevents the user from rotating the safety cap 90 further in the given direction and indicates to the user that the safety cap 90 is in a passage position. However, it will be appreciated that this predetermined degree of rotation can be set to another angle, for example 90° or 180°, by altering the relative position of the aforementioned components and the spacing between the two longitudinal stops 96. Indeed, for a rotation up to 360°, the rotation is in one direction.

This 160° twisting action breaks the frangible connection 94 between the safety cap 90 and the forward surface 60 of the lancet body 60. The safety cap 90 is now in the passage position because the abutment projection 29 can travel longitudinally in a longitudinal channel 97 branching off from the annular slot 95 (i.e. there is a gap in the ledge 95' formed by the longitudinal channel 97 through which the abutment projection can pass by pulling the graspable portion of 91 the safety cap 90 in the pricking direction P). Thus, the cap 90 can be freed from the passage 19 of the housing body 20. Withdrawal of the cap 90 in the pricking direction P exposes the sharp tip 53 inside the housing 10. Until this time the needle 52 is encased in sealed plastic to ensure the sterility thereof prior to use and removal of the safety cap 90 is prevented before the frangible connection 94 between the safety cap 90 and the lancet 50 is broken.

Figure 2:
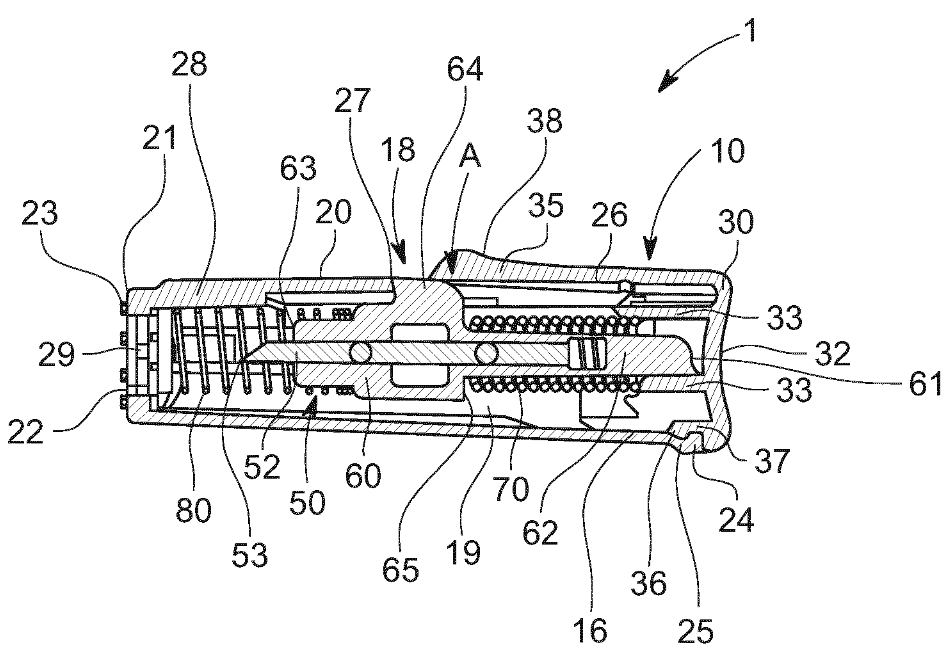
FIG. 2 is a longitudinal cross-sectional side view of the blood sampling device of FIG. 1 with the cap removed and with the lancet in a primed position.

Referring to FIG. 2, once the cap 90 has been removed from the housing body 20, the blood sampling device 1 is primed and the lancet 50 is ready to be fired. The boss 64 on the lancet body 60 abuts the detent 27 on the housing body 20 preventing forward movement of the lancet body 60 in the passage 19. The boss 64 on the lancet body 60 is visible to the user in the window 18. The user can therefore see that the lancet 50 is in a primed position with the forward surface of the boss 64 abutting the detent 27. The user can therefore see that the device 1 is primed and ready to be fired.

The cap 90 is no longer preventing deflection of the lancet 50 within the passage 19 of the housing body 20. In use, the user will hold the front face 21*a* of the blood sampling device 1 against the skin, position their thumb or finger on the finger pad 38 and depress the trigger member 35 in an actuation direction A (transverse to the longitudinal axis of the passage 19) from a rest position to a fire position. This is enabled because the cap 90 is no longer preventing deflection of the lancet 50. Initial depression of the trigger member 35 flexes it inward into the passage 19 of the housing body 20 such that the lower surface of the trigger member 35 contacts the boss 64 of the lancet body 60. Further depression of the trigger member 35 forces the boss 64 (and therefore the entirety of the forward portion of the lancet body 60) downwards within the passage 19.

Figure 3:
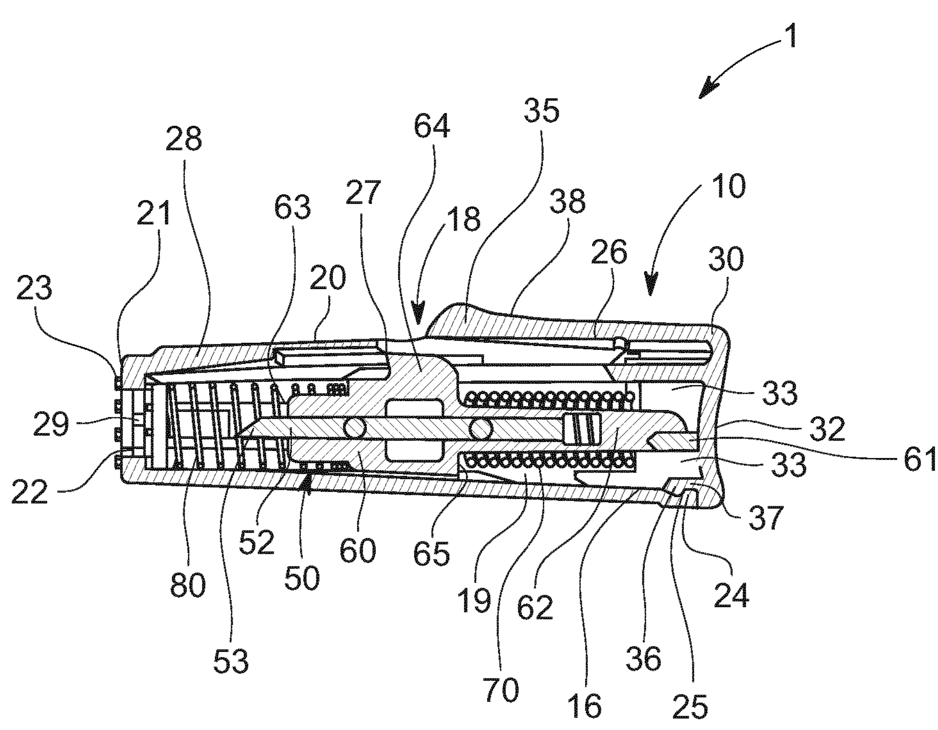
FIG. 3 is a longitudinal cross-sectional side view of the blood sampling device of FIG. 1 after actuation of the trigger member.

Referring to FIG. 3, when the trigger member 35 is depressed into the fire position, the forward surface of the boss 64 is moved out of engagement with the detent 27 such that it is no longer abutting the detent 27 (i.e. the forward surface of the boss 64 and the detent 27 are not radially aligned). Although not shown by FIG. 3, the boss 64 on the lancet body 60 pivots about a contact point between the tail 62 of the lancet body 60 and the oblong wall 33 on the housing end cap 30. Therefore, the lancet body 60 is angularly positioned relative to the longitudinal axis of the housing 10 and the lancet body 60 is no longer blocked by the detent 27.

Figure 4:
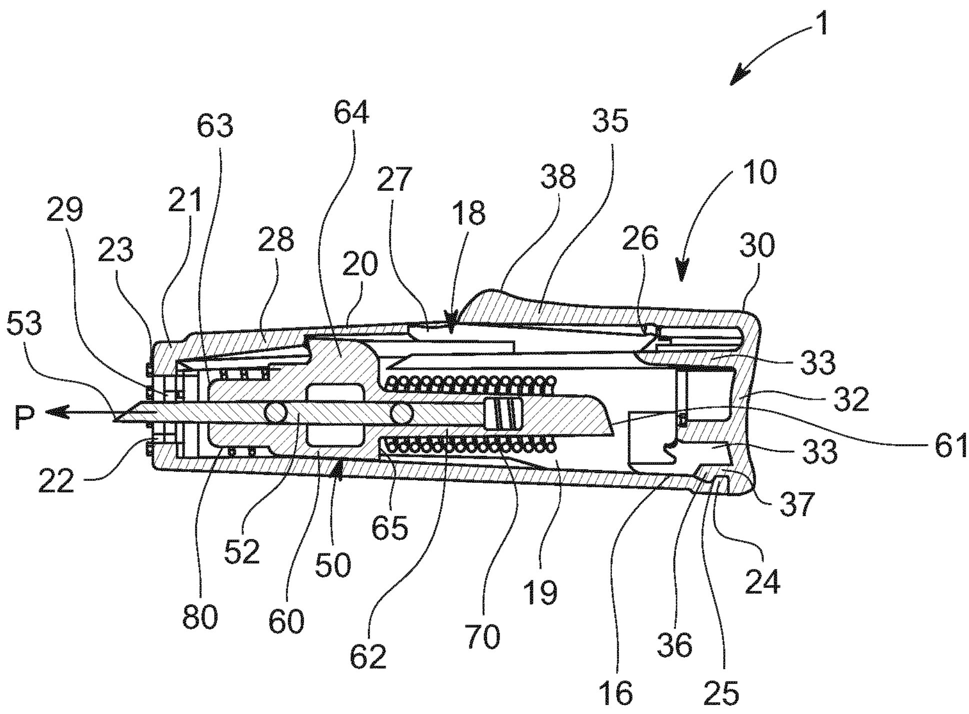
FIG. 4 is a longitudinal cross-sectional side view of the blood sampling device of FIG. 1 with the lancet in a lancing position.

Referring to FIG. 4, once the forward portion of the lancet body 60 has been radially deflected within the housing out of abutment with the rear surface of the detent 27, there is no obstacle blocking forward movement of the lancet body 60 within the passage 19 (i.e. the lancet body 60 is in a passage position). Thus, the drive spring 70 urges the lancet body 60 forwardly in the pricking direction P. This forward movement is against the force of the return spring 80 such that the return spring 80 is compressed. This is enabled because the drive spring 70 is stronger than the return spring 80.

Figure 8:
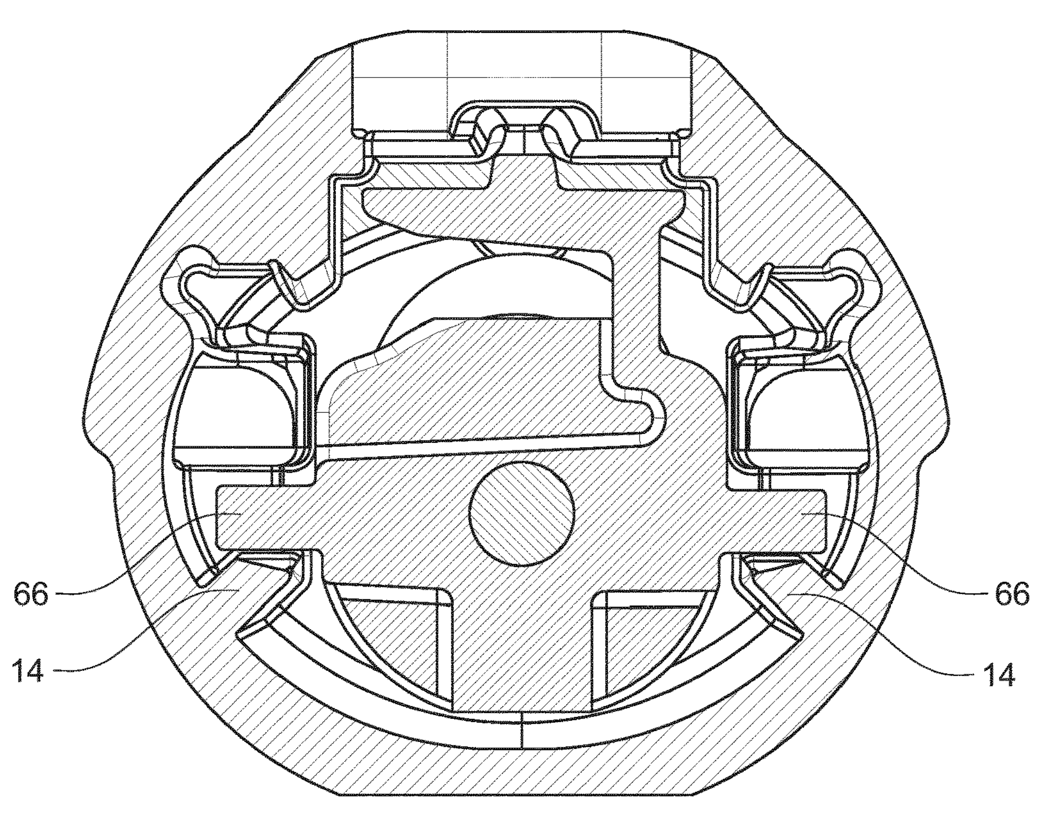
FIG. 8 is a cross-section through the housing, illustrating the position of the lancet during firing

Alignment of the lancet body 60 within the passage 19 is obtained by the radial wings 66 of the lancet body 60 contacting a track or inner projection 14 of the housing wall as shown in FIG. 8. The forward portion of the track to obtain alignment of the lancet body during the lancing motion extends along a forward portion of the housing.

The lancet body 60 continues to travel forwardly within the passage 19 under the bias of the spring 70 until the boss 64 contacts the rear surface of the passage rib 28, preventing further forward movement of the lancet body 60. The sharp tip 53 protrudes from the front face 21*a* of the housing 10 out of the aperture 22, to puncture the skin of the user, drawing a sample of blood from the user.

When the lancet body 60 is in a pricking position (FIG. 4), the drive spring 70 is fully expanded. As the drive spring 70 is freely mounted in the housing body 20 (neither end of the drive spring 70 is fixed to the lancet body 60 or the end cap 30), the drive spring 70 continues to move forwardly in the passage 19 under its own momentum even after the drive spring 70 has ceased to act on the lancet 50. As such, the forward end of the drive spring 70 is no longer urging the rear surface 65 of the lancet body 60 forwardly in thee passage 19 and the rearward end of the drive spring 70 is no longer urged against, or contacting, the housing end cap 30.

Figure 5:
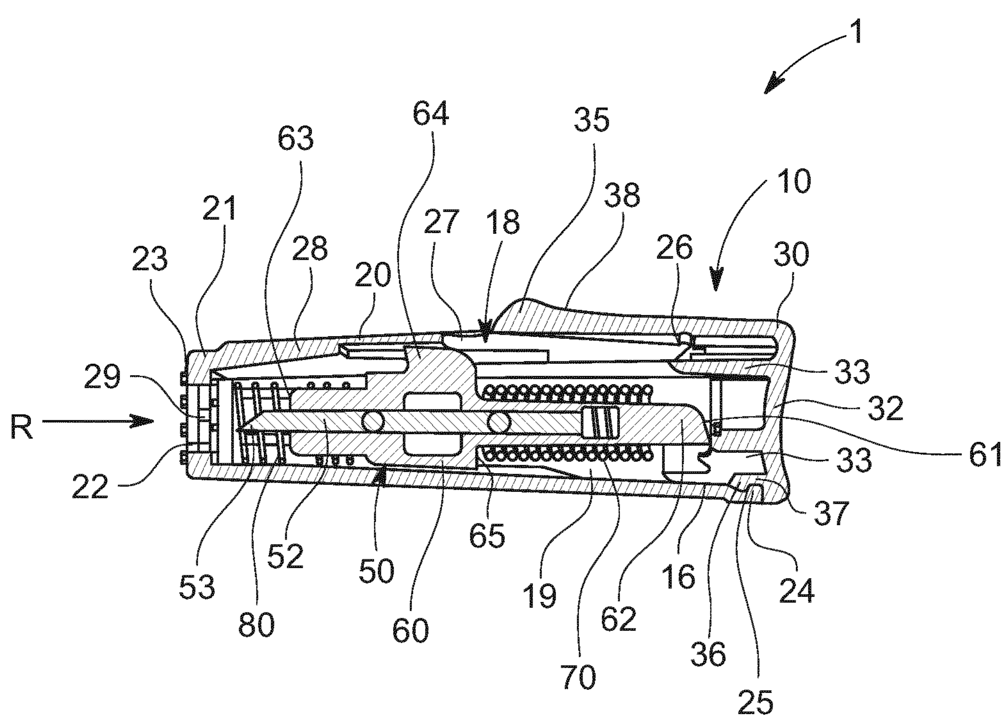
FIG. 5 is a longitudinal cross-sectional side view of the blood sampling device of FIG. 1 with the lancet in a safe position after completion of firing.

Referring to FIG. 5, the forwards movement of the lancet 50 in the passage 19 has compressed the return spring 80. Once the boss 64 contacts the rear surface of the passage rib 28, forward movement of the lancet 50 is arrested. The lancet 50 is then urged rearwardly in a return direction illustrated by arrow R in the passage 19 by the return spring 80. This returns the sharp tip 53 safely within the housing 10 to prevent accidental injury but with the lancet 50 well forward of the initial primed position. The extent to which the lancet 50 is driven backwards in the return direction R is determined by the relative strength of the return spring 80 and the drive spring 70. The relative strength is such that the return spring 80 moves the lancet 50 back just far enough such that neither the drive spring 70 nor the return spring 80 are loose within the housing passage 19 (i.e. so that they do not rattle around). The return spring 80 also prevents the sharp tip 53 from projecting forwardly from the aperture 22 if the blood sampling device 1 is tilted with the forward end facing downwards. This further protects the user from needle stick injuries after the blood sampling device 1 has been used.

After firing, the boss 64 of the lancet body 60 is no longer visible via the window 18. The absence of the lancet body 60 in the window 18 indicates to the user that the blood sampling device 1 has been fired and should be disposed of.

After completion of lancing, the user will remove the blood sampling device 1 from the surface of the skin. As noted above, the sharp tip 53 will be safely positioned within the passage 19 of the housing body 20. However, the user may try to re-prime the blood sampling device 1 such that it can be re-used by re-inserting the cap 90 into the housing body 20 and applying a force in the rearward direction R against the cap 90 to urge the lancet body 60 rearwardly in the passage 19. This is prevented by a number of separate features. Firstly, it is difficult to re-insert the safety cap 90 into the passage 19 via the aperture 22. This is because the safety cap 90 has to be in a given rotational orientation relative to the housing body 20 for re-insertion of the safety cap 90 to be possible. More specifically, re-insertion of the safety cap 90 will only be possible if the safety cap 90 is in the passage position, with the elongate longitudinal channels 97 on the safety cap 90 in radial alignment with the abutment projection (tooth) 29 on the passage 19.

If the user is able to re-insert the lancet cap 90 backwards into the passage 19, the oblong wall 33 projecting substantially perpendicularly from the base 32 of the end cap 30 contacts a rear face 61 of the tail 62. Due to the contact angle of the two components, the oblong wall 33 deflects the lancet 50 downwards in the passage 19. This prevents the lancet 50 from being moved back far enough in the passage 19 for the boss 64 on the lancet body 60 to re-engage with the detent 27 on the housing body 20.

The drive spring 70 may also shift laterally from its original position such that it blocks rearwards movement of the lancet body 60 to prevent re-priming of the device 1.

Figure 9:
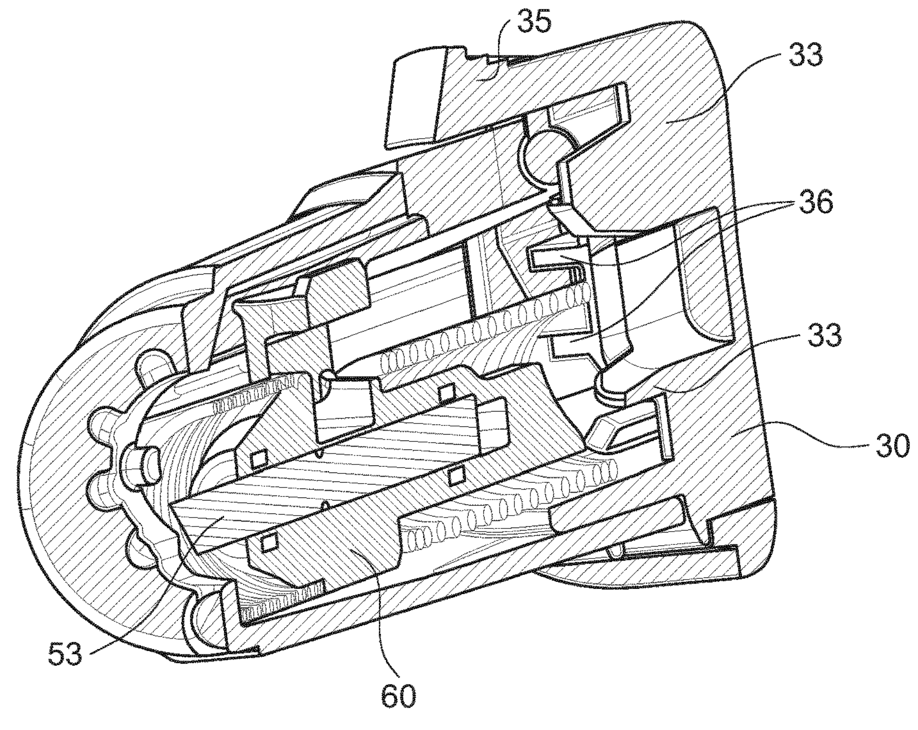
FIG. 9 is a longitudinal cross-section through the device after firing illustrating the ribs present in the end cap.

Additionally, as illustrated in FIG. 9 the end cap may be provided with one or more ribs 34 which project into the housing from the end cap 30. These ribs are positioned to further constrain the area into which the tail 62 of the lancet body 60 must fit in order for the device 1 to be re-primed. Preferably they are positioned such that, even if the tail 62 is deflected above the oblong wall 33, the tail 62 will come into contact with one of the ribs.

Embodiment 2

Referring to FIGS. 10 to 17, a blood sampling device 201 according to a second exemplary embodiment of the present invention comprises the same features and works in the same way as the blood sampling device 1 of the first exemplary embodiment. Therefore, unless stated otherwise, the description of the first embodiment applies equally to the second embodiment. As such, like features will be denoted with like reference numerals but starting from 200.

A blood sampling device 201 according to a second exemplary embodiment of the present invention includes a plastic housing 210 containing a lancet 250, a drive spring 270 and a return spring 280. Both the drive spring 270 and the return spring 280 are compression springs.

The housing 210 is formed of two main components; a first housing member which is a housing body 220 and a second housing member which is a housing end cap 230. The housing body 220 is an injection moulded plastic component forming a longitudinal cylindrical receptacle having a planar front face 221 defining a circular aperture 222 therein. Projecting from the front face 221 in an annular array around the aperture 222 are a plurality of projections 223 which are designed to stimulate the skin to 'confuse' the nerve endings and alleviate the perceived pain experienced when the lancet tip 253 penetrates the skin to make an incision. The rear end 224 of the housing body 220 is open with an oval-shaped cross-section to receive the internal components of the blood sampling device 201 during assembly. Spaced forwardly from the circumferential edge of the rear end 224 and on an internal surface 16 of the housing body 20 is a circumferential notch 225. Extending forwardly from the open rear end 224 and forming a gap in the circumferential notch 225 is an elongate cut-out 226 having a substantially rectangular shape. The forwardmost edge of the cut-out 26 is curved and forms a detent 227.

Figure 16:
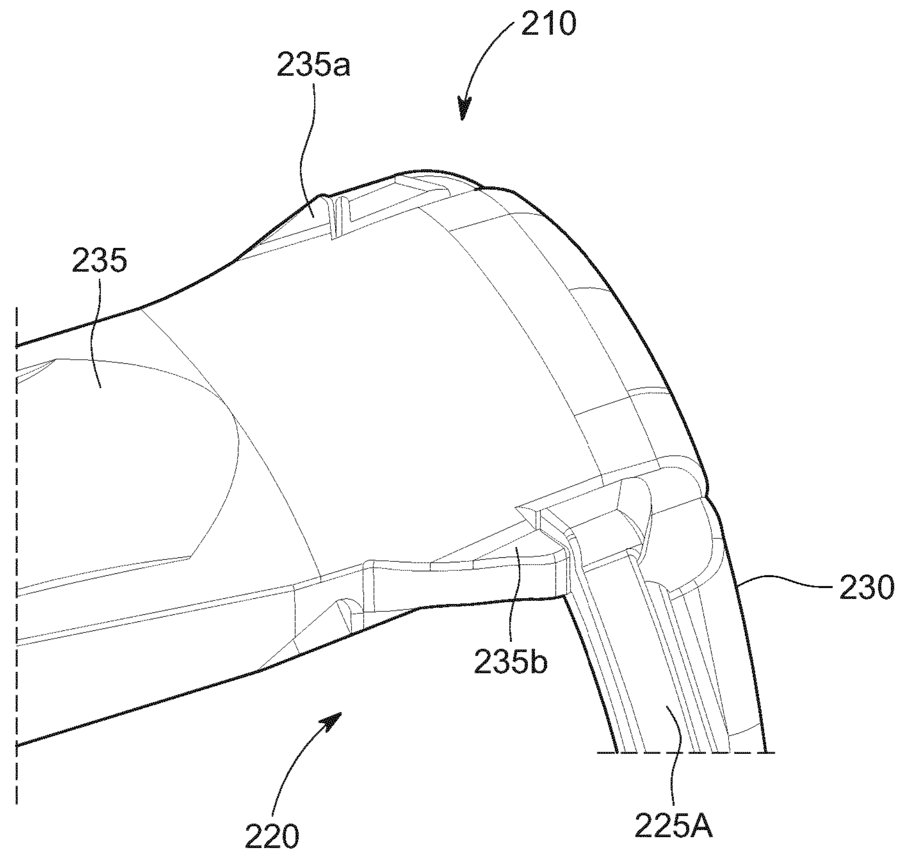
FIG. 16 is a perspective view of the rearward end of the housing of the blood sampling device of FIG. 10.

Referring specifically to FIG. 16, the housing body 220 also comprises an external, circumferential rib 225A extending around the rearward end 224 thereof having a gap formed by the elongate cut out 226.

The internal surface 216 of the housing body 220 defines a passage 219. The internal surface 216 of the housing body 220 comprises a longitudinal rib 228 projecting into the passage 219 and extending rearwardly from the front 221 of the housing body 220. The aperture 222 in the front face 221 of the housing body 220 also comprises a pair of diametrically opposed radial abutment projections (teeth) 229 which project into the bore of the aperture 222 to provide a narrowed portion of the aperture 222 having a reduced diameter.

The housing end cap 230 is an injection moulded plastic component comprising a base 232 having a curved central indentation. The housing end cap 230 has a circumferential wall 237 extending perpendicularly to the base 232 around the periphery of the base 232 which has a longitudinal gap (not shown) therein. An elongate trigger member 235 having a textured (ribbed) outer surface 238 extends substantially perpendicularly from the base 232, passing through the gap in the wall 237 of the end cap 230. The trigger member 235 also comprises a pair of wing clips 235*a* and 235*b* which extend radially outwardly from the elongate trigger member 235. The distance between the outermost edges of the wing clips 235*a*, 235*b* is larger than the width of the elongate cut out 226.

An outwardly protruding engagement rib 236 extends around the circumferential forward edge 237' of the wall 237 of the housing end cap 230. The engagement rib 236 is shaped and dimensioned to form a snap fit in the notch 225 of the housing body 220. As the wall 237 fits flush to the internal surface 216 of the housing body 220 and the engagement rib 236 forms a snap fit with the notch 225 of the housing body 220, they assist in guiding the housing end cap 230 into the open end 224 of the housing body 220 during assembly and stabilising the housing end cap 230 in the housing body 220 after assembly. An oblong walled portion 233 projects substantially perpendicularly from the base 232 and is spaced radially inwardly from the circumferential edge thereof to define a recess within which the rear end of the lancet tail 262 sits in the initial assembled configuration.

The blood sampling device 201 of the second exemplary embodiment of the present invention differs from the first embodiment of the present invention in that it comprises an anti-deflection means configured to prevent the trigger member 235 from being actuated and the lancet body 260 from being deflected away from the longitudinal axis of the passage 219 both when the lancet 250 is in the pre-primed position and during removal of the safety cap 290 from the housing body 220.

Figure 11:
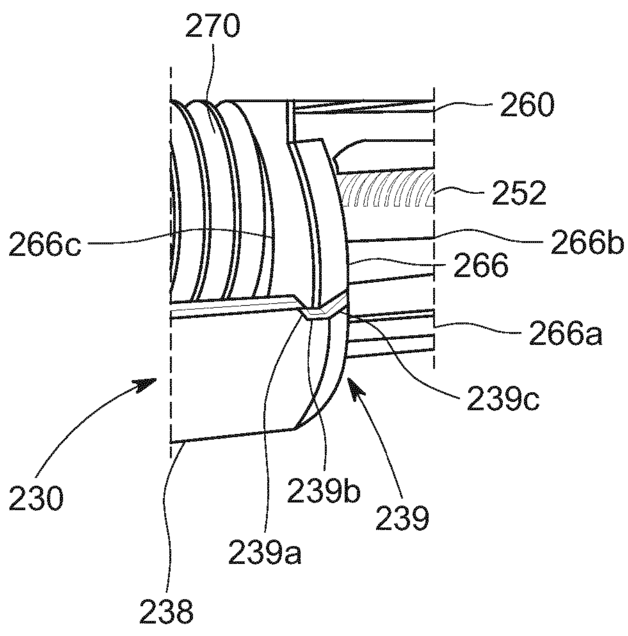
FIG. 11 is a schematic side view of the lancet body and end cap leg of the blood sampling device of FIG. 10 in the initial assembled configuration.
Figure 13:
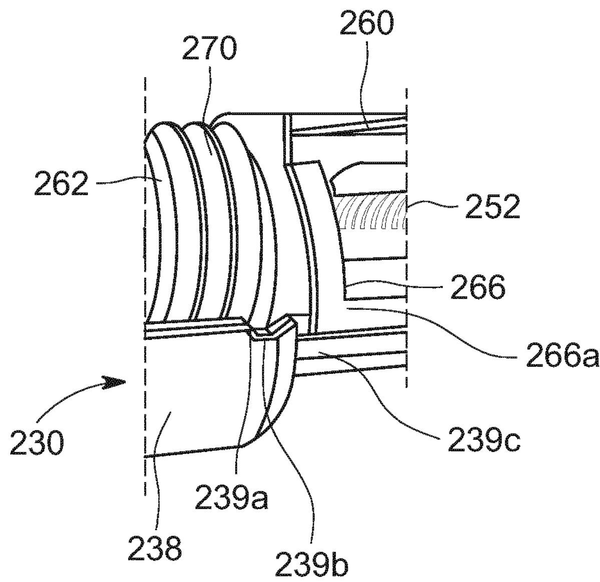
FIG. 13 is a schematic side view of the lancet body and end cap leg of the blood sampling device of FIG. 10 when the cap is removed and the lancet is in the primed configuration.
Figure 14:
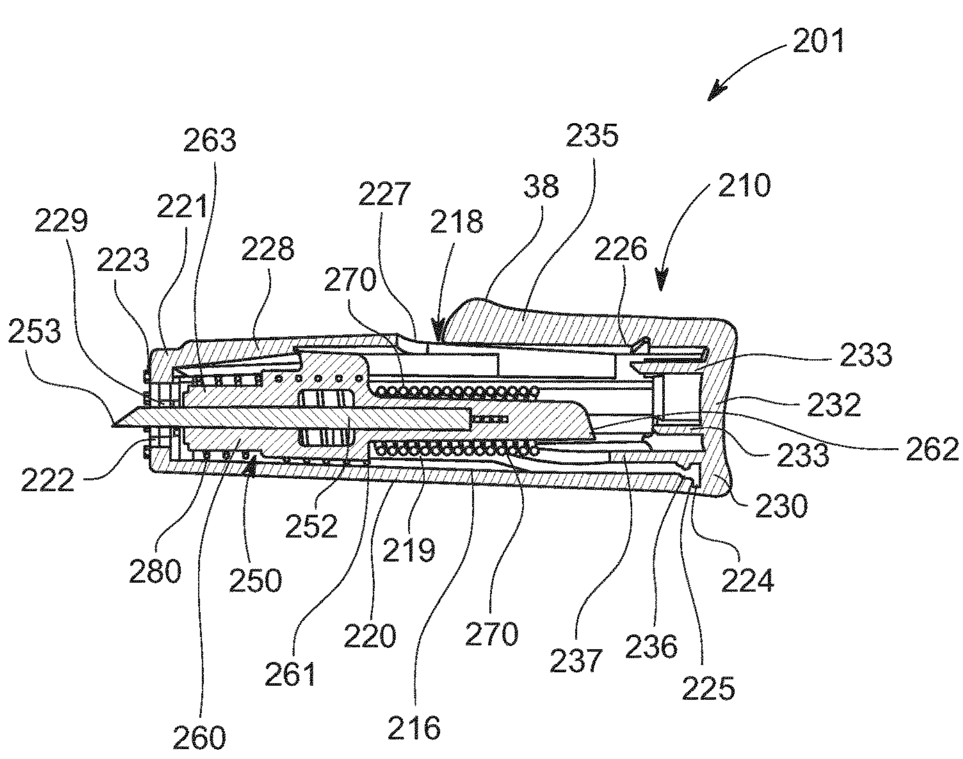
FIG. 14 is a longitudinal cross-sectional side view of the blood sampling device of FIG. 10 with the lancet in a lancing position.
Figure 15:
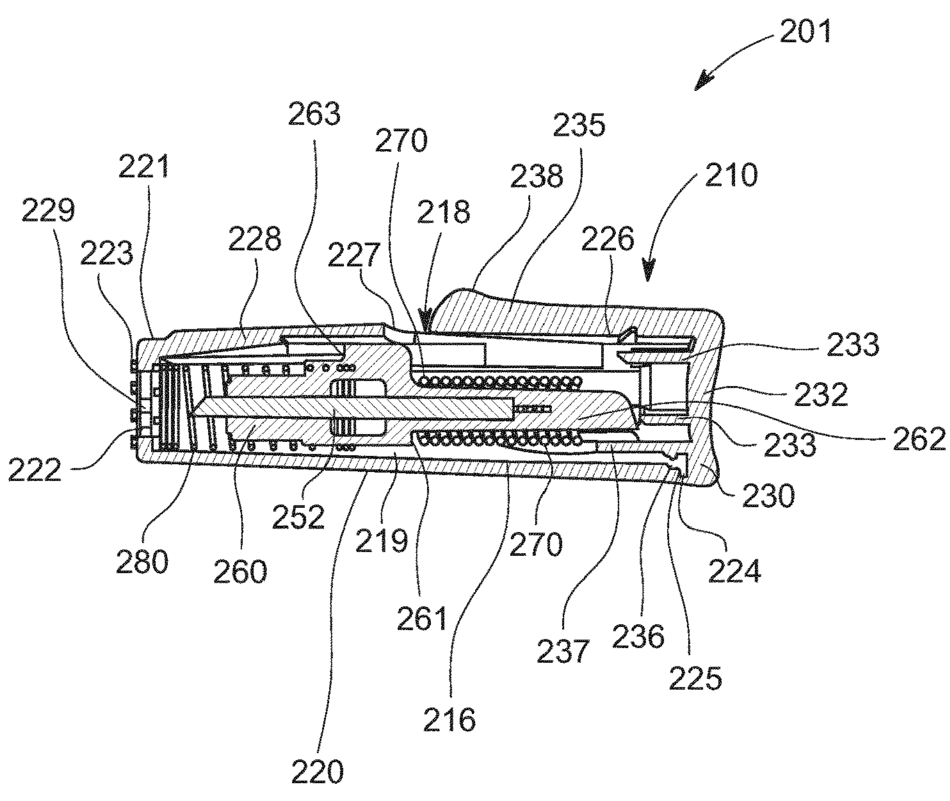
FIG. 15 is a longitudinal cross-sectional side view of the blood sampling device of FIG. 10 with the lancet in a safe position after completion of firing.

Referring to FIGS. 11 and 13 specifically, the housing end cap 230 comprises an elongate longitudinal leg 238 projecting substantially perpendicularly from the base 232 diametrically opposite and substantially parallel to the trigger member 235. The leg 238 is curved to accommodate the curvature of the lancet body 260 which is located adjacent thereto in the initial assembled configuration. The forward end of the leg 238 comprises a pair of recesses 239, one located at the front of each longitudinal edge of the curved leg 238. Each recess 239 has a flat base 239*b* connected at right angles to a rear surface 239*a* and a forwardly sloping front surface 239*c*.

The lancet body 260 comprises a pair of wings 266 which project horizontally in the device at an angle of roughly 90° from the immediately adjacent surfaces of the lancet body 260. Each wing 266 has a planar front surface 266*b* and rear surface 266*c* and the lower surface 266*a* thereof is angled to slope rearwardly so as to compliment the forwardly sloping front surface 239*c* of each recess 239 on the leg 238 of the end cap 230.

The lancet 250 comprises a lancet body 260 moulded around a needle 252, the sharp tip 253 of the needle 252 projecting from a forward surface 263 of the lancet body 260. The lancet body 260 also comprises a boss 264 projecting from the upper surface thereof. The rear surface 265 of the lancet body 260 has an elongate rearwardly extending tail 262 projecting therefrom.

Figure 10:
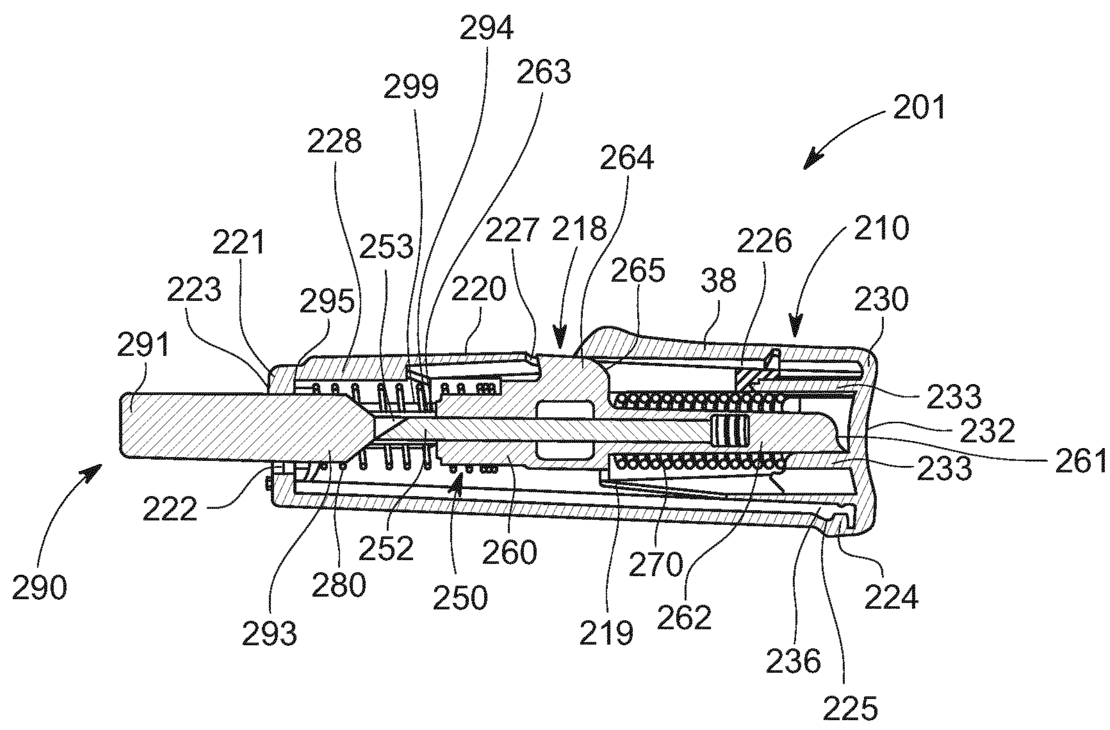
FIG. 10 is a schematic longitudinal cross-sectional side view of a blood sampling device according to a second exemplary embodiment of the present invention in an initial assembled configuration with the lancet in a pre-primed position.

Referring to FIG. 10, an elongate safety cap 290 is integrally moulded with the forward surface 263 of the lancet body 260 such that the lancet needle 252 is initially concealed within the safety cap 290 to maintain the sterility of the needle 252 prior to use.

Figure 17A:
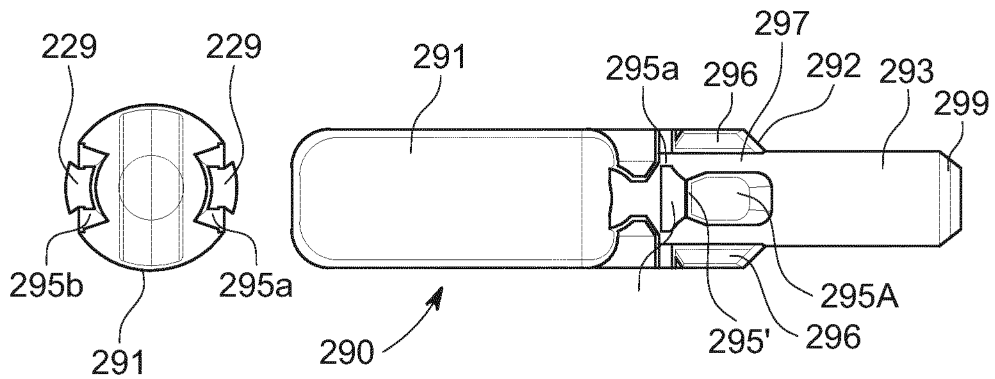
FIG. 17 is a schematic side view of a safety cap of a blood sampling device of FIG. 10 showing the sequential movement of the safety cap from A) a blocked position; to B) a passage position; to C) a passage position in which the safety cap is being removed.
Figure 17B:
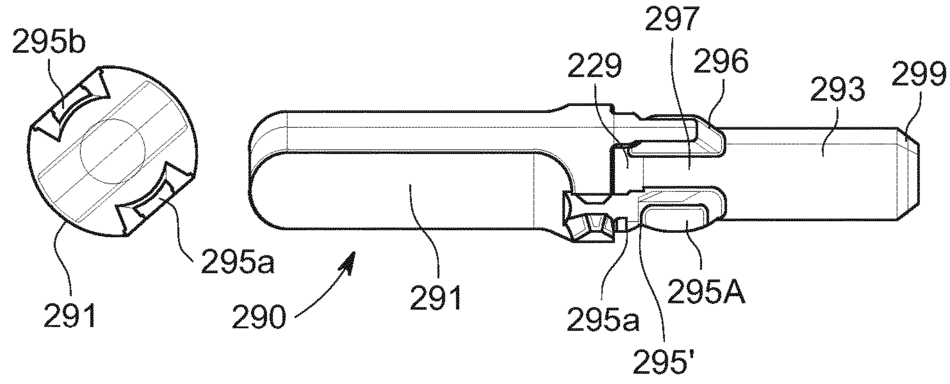
Figure 17C:
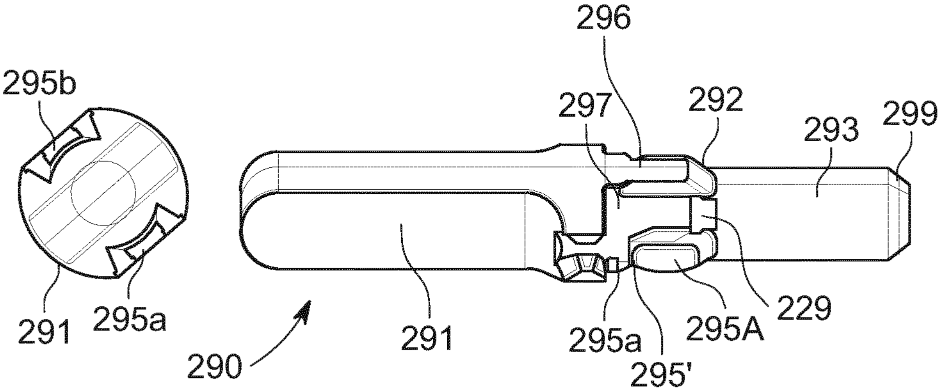

Referring specifically to FIG. 17, the safety cap 290 differs from that of the first embodiment. The safety cap 290 has a graspable portion 291 at a first forward end thereof having a flat, substantially cuboid shape, which is connected to a stem 293 having a substantially cylindrical shape at a second rearward end thereof. The stem 293 of the safety cap 290 comprises a conical portion 299 which narrows towards a connection point 294 which connects the safety cap 290 to the forward surface 263 of the lancet body 260 such that the two components are frangibly connected. The conical portion 299 focusses the torsion when the safety cap 290 is twisted relative to the lancet 250 on the connection point 294, making it easier to break the frangible connection 294 so that the safety cap 290 can be removed.

The safety cap 290 comprises an annular slot 295 which is shaped and dimensioned to receive the two abutment projections (teeth) 229 on the aperture 222 of the housing body 220 when the device 201 is in an initial assembled configuration. However, in this embodiment, the stem 293 of the safety cap has the same diameter as the annular slot 295. A pair of diametrically opposed protrusions 295A are formed on the stem 293 adjacent the rearward edge of the annular channel 295. The forward surface of each of the protrusions 295A forms a ledge 295' on the stem 293 of the safety cap 290 having an increased diameter relative to the annular slot 295. The annular slot 295 has two longitudinal stops 296, spanning the width of the annular slot 295 and extending rearwardly along the external surface 293' of the stem 293. The stops 296 diametrically opposed with gaps between them of about 120-160° on either side of the stem 293 of the lancet cap 90. Thus, the annular slot 295 comprises a first arcuate segment **295*a* on a first side of the stem 293 between the stops 296 and a second arcuate segment 295*b* of the opposing side of the stem 293 between the stops. The skilled person would be aware that this spacing could be modified by changing the width of the stops 296 depending on the desired degree of rotation of the safety cap 290 prior to removal of the safety cap 290 and that the second arcuate segment is not necessarily required. Extending rearwardly from the annular slot 295 on either side of each stop 296 is a pair of elongate longitudinal channels 297**.

The blood sampling device 201 is assembled in a similar way as the blood sampling device 1 of the first embodiment. Firstly, the return spring 280 is dropped into the housing body 220 via the rearward end 224 of the housing body 220. As the return spring 280 is a compression spring, the rotational orientation of the return spring 280 in the housing body 220 does not matter, i.e. the return spring 280 can be located in the housing body 220 in any rotational orientation. The return spring 280 is not physically inter-connected with any components in the housing body 220.

Secondly, the safety cap 290 and frangibly connected lancet 250 are dropped into the housing body 220 via the rearward end 224 of the housing body 220. The graspable portion 291 of the safety cap 290 is dimensioned such that it can pass through the circular aperture 222 in the front face 221 of the housing body 220 such that it is located outside of the housing 210 in the initial assembled configuration. The lancet 250 is rotationally aligned so that the boss 264 on the lancet body 260 is located within elongate cut-out 224 in the housing body 220. However, in this embodiment, the forward surface of the boss 264 is located rearwardly of the detent. In this rotational orientation, the safety cap 90 is in a blocked position, the opposing protrusions 295A of the safety cap 290 abuts the opposing abutment projections (teeth) 229 which project into the bore of the aperture 222 of the housing body 220. This prevents forward movement of the safety cap 290 and frangibly connected lancet 250 in the housing. Therefore, the stem 293 of the safety cap is located in the passage 219 in the initial assembled configuration.

Thirdly, the drive spring 270 is dropped into the housing body 220 via the rearward end 224 of the housing body 20 such that it surrounds the rearward tail 262 of the lancet body 260. As the drive spring 270 is a compression spring, the rotational orientation of the drive spring 270 in the housing body 220 does not matter, i.e. the drive spring 270 can be located in the housing body 220 in any rotational orientation. The drive spring 270 is not physically interconnected with any components in the housing body 220.

Finally, the housing end cap 230 is rotationally aligned with the housing body 220 such that the trigger member 235 is aligned with the elongate cut-out 226 in the housing body 220 (i.e. located radially above the elongate cut-out 226 and the boss 264 on the lancet body 260). The end cap 230 is placed over the lancet tail 262 such that the rear end of the lancet tail 262 is located in the recess formed by the oblong walled portion 233 on the base 232 of the end cap 230. As such, the housing end cap 230 interacts with the lancet 250 before the housing body 220, ensuring that end cap 230 assembles in the correct position in relation to the lancet 250.

Due to the elongate cut out 226, the rearward end 224 of the housing has a degree of resilient deformability such that the elongate cut out 226 can flex outwardly around the outermost edges of the wing walls **235*a*, 235*b* when the housing end cap 230 is pushed in to the rear end 224 of the housing body 220 and snap back in when the end cap 230 is fully inserted. As such, when the housing end cap 230 is pushed in to the rear end 224 of the housing body 220, the engagement rib 236 of the end cap 230 forms a snap fit in the notch 225 of the housing body 220 (as per the first embodiment) and the wing clips 235*a*, 235*b* also latch on to the circumferential rib 225A at the rear of the housing body 220. This further prevents removal of the end cap 230 from the housing body 220, increasing the force required to remove the end cap 230 and thus the trigger member 235 from the device 201. This improves the safety of the device 201, preventing the user from accessing the internal components of the device 201**.

However, the blood sampling device 201 of the second embodiment differs from the blood sampling device of the first embodiment in that the lancet 250 comprises not only a primed position but also comprises a pre-primed position in which the lancet body 260 is positioned such that the boss 264 on the lancet body 260 is rearward of the detent 227 on the housing body 220 (i.e. it is not contacting the detent 227). In this pre-primed position, there is a gap or window 218 between the forwardmost surface of the trigger member 235 and the detent 227 such that the user can see that the boss 264 on the lancet body 260 is rearward from the detent 227 on the housing body 220 (i.e. there is a gap between them). The user can therefore identify that the lancet 250 is in the pre-primed position.

Once the device 201 has been assembled, the longitudinal leg 238 contacts the wall of the passage 219 diametrically opposite the trigger member 235 at the rearwardmost end thereof and projects into the passage 219 at the forward end thereof. As such, the rearward portion of the passage 219 has a reduced diameter along the section in which the longitudinal rib 238 extends. The skilled person would understand that the elongate longitudinal rib 238 may alternatively be an integrally formed protrusion on the wall of the passage 219 without affecting the function thereof.

When the device is in the initial assembled configuration, lancet 250 is held against forward movement because the abutment projections 229 on the housing body 220 are located in the annular slot 295 on the safety cap 290. The two abutment projections 229 are radially aligned with the ledges 295' formed by the two protrusions 295A on the stem 293 of the safety cap 290, preventing forward movement of the lancet cap 290 relative to the housing body 220 and thus removal of the safety cap 290 from the housing body 220. The lancet body 260 is positioned such that the boss 264 on the lancet body 260 is rearward of the detent 227 on the housing body 220 (i.e. it is not contacting the detent 227). This is a pre-primed position. In this pre-primed position, there is a gap or window 218 between the forwardmost surface of the trigger member 235 and the detent 227 such that the user can see that the boss 264 on the lancet body 260 is rearward from the detent 227 on the housing body 220 (i.e. there is a gap between them). The user can therefore identify that the lancet 250 is in the pre-primed position.

In the pre-primed position, the lancet body 260 contacts the longitudinal leg 238 such that the lancet body 260 cannot be deflected downwardly in the passage 219. This in turn means that the trigger member 235 cannot be depressed in an actuation direction transverse to the longitudinal axis of the passage 219 from a rest position to a fire position. More specifically, if a user tries to depress the trigger member 235, it will contact the lancet body 260, pushing each of the lancet wings 266 against each of the respective recesses 239 in the longitudinal leg 238, preventing further transverse movement of the lancet body 260 in the passage 219. Thus, the trigger member 235 cannot be fully depressed to actuate the device 201 and the lancet body 250 cannot be deflected transverse the longitudinal axis. As such, the boss 264 on the lancet body 260 cannot be deflected past the detent 227 when the lancet 250 is in the pre-primed position or until the safety cap 290 has been removed from the passage 219. This also limits the relative angular movement between the safety cap 290 and the lancet 250 about the frangible connection 294 preventing the frangible connection 294 from breaking before deliberate rotation of the safety cap 290. This in turn reduces the chances of the needle 252 bending or losing sterility prior to use.

As the lancet body 260 is constrained against rotation relative to the passage 219 by the location of the boss 264 in the elongate cut-out 226, twisting the safety cap 290 relative to the housing body 220 about the direction of pricking P rotates the safety cap 290 relative to the lancet 250. Rotation of the safety cap 290 relative to the housing body 220 is enabled as the annular slot 295 accommodates the abutment projections 229 as the safety cap 290 rotates. However, rotation of the safety cap 290 relative to the housing body 220 is only enabled to a certain predetermined degree until the abutment projections 229 contact the stops 296 in the annular slot 295 preventing further relative rotational movement. The predetermined degree of rotation is set by the relative positions of the abutment projections 229 on the housing body 220 and the position of the stops 296 in the annular slot 295 in the initial assembled configuration. In this case, the safety cap 290 can be rotated by roughly 60° in either direction from the initial assembled configuration in which it is in a blocked position until the abutment projections 229 contact the respective stops 296.

This 60° twisting action breaks the frangible connection 294 between the safety cap 290 and the lancet body 260. The safety cap 290 is in the passage position because the abutment projections 229 can travel longitudinally in respective longitudinal channels 297 branching off from the annular slot 295 (i.e. there is a gap in the ledge 295' formed by the longitudinal channel 297 through which the abutment projection can pass by pulling the graspable portion of 291 the safety cap 290 in the pricking direction P). Thus, the cap 290 can be freed from the housing body 220. Withdrawal of the cap 290 in the pricking direction P exposes the sharp tip 253 inside the housing 210. Until this time the needle 252 is hermetically sealed prior to use and removal of the safety cap 290 is prevented before the frangible connection 294 between the safety cap 290 and the lancet 250 is broken.

If the user presses the trigger 235 whilst the safety cap 290 is being removed, the base of the trigger 235 will contact the lancet body 260, pushing each of the lancet wings 266 against each of the respective recesses 239 in the longitudinal leg 238, preventing further transverse movement of the lancet body 260 in the passage 219. The angled lower surface 266*a* of each of the lancet wings 266 engages each respective recess 239 on the leg 238 of the end cap 230, preventing forward movement of the lancet body 260 in the passage 219 whilst the safety cap 290 is being removed. This frictional engagement stops the lancet body 260 from being released and being urged forwardly in the passage 219 under the force of the drive spring 270 until pressure is removed from the trigger member 235 by the user. When pressure is removed from the trigger member 235, frictional engagement between the lower surface 266*a* of each of the lancet wings 266 and the respective recesses 239 on the leg 238 will also be removed such that the angled lower surface 266*a* of each of the lancet wings 266 can pass over the angled forward surfaces 239*c* of the recesses 239 under the force of the drive spring 270. The lancet body 260 will then move forwardly into the primed position in which the boss 264 on the lancet body 260 abuts the detent 227 on the housing body 220 preventing forward movement of the lancet body 260 in the passage 219 in the same way as if the trigger member 235 had not been depressed during removal of the safety cap 290 as described below.

The skilled person would be aware that the recesses 239 in the longitudinal leg 238 assist in engaging the angled lower surface 266*a* of each of the lancet wings 266. However, this feature is not necessary and planar surfaces as illustrated in FIG. 18 would be sufficient to prevent forward movement of the lancet body 260 in the passage 219 whilst the safety cap 290 is being removed due to the frictional engagement therebetween when the trigger member 235 is being depressed.

Figure 18:
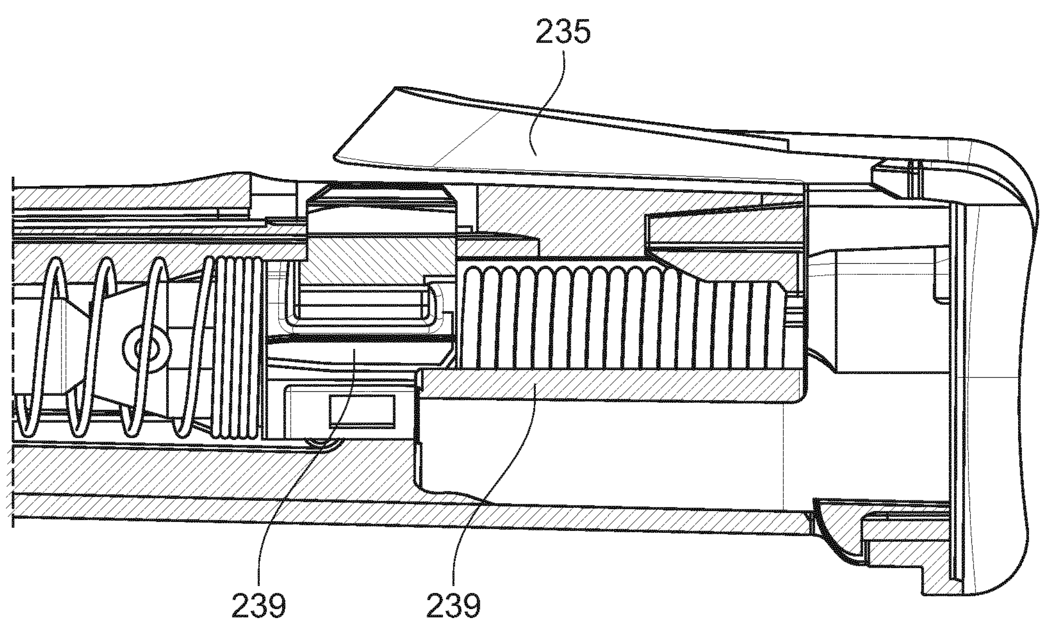
FIG. 18 is a longitudinal cross-section of a blood sampling device of FIG. 10 in the pre-primed position.
Figure 19:
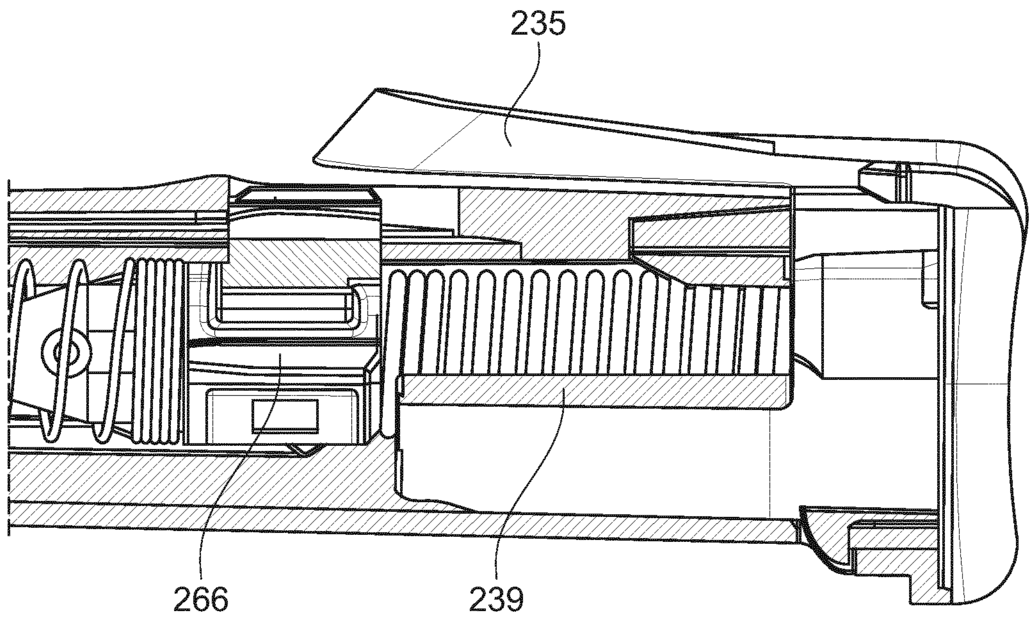
FIG. 19 is a longitudinal cross-section of a blood sampling device of FIG. 10 in the primed position.

FIG. 18 Illustrates a lancet in a pre-primed position. The lancet has a planar track 239. The planar track 239 may be present as a moulding within the housing 21 or be present on the housing end cap 30. At least a part, in this instance the rear end, of the wings 266 rests upon the track 239 such that if the trigger member 235 is depressed the lancet cannot be fired as depression of the lancet is prevented by the wings. When the safety cap is removed the lancet moves to a primed position as shown in FIG. 19 where the wings are no longer in contact with the track and therefore depression of the trigger is not inhibited. The planar track 239 may be separate from the forward track described with reference to Embodiment 1. Alternatively, a single track may be provided having two sections, a rearward section and a forward section.

Figure 12:
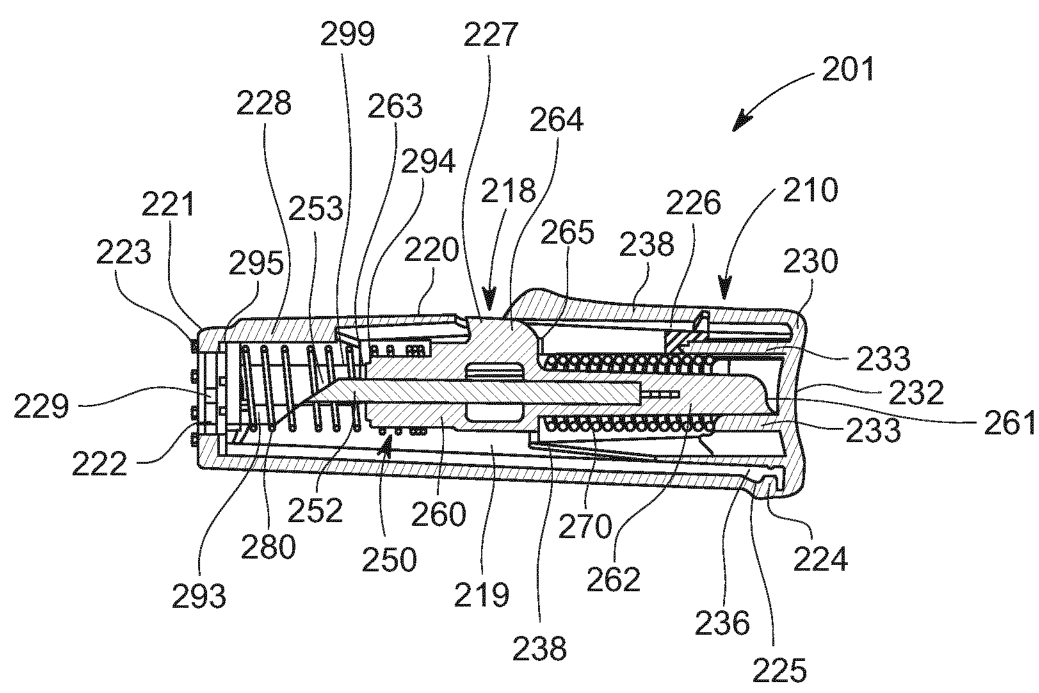
FIG. 12 is a is a longitudinal cross-sectional side view of the blood sampling device of FIG. 10 with the cap removed and with the lancet in a primed position.

Referring to FIGS. 12 and 13, once the safety cap 290 has been removed from the passage 219 and pressure is removed from the trigger member 235 if it has been depressed during removal of the safety cap 290, the lancet 250 is urged forwardly in the passage 219 under the force of the drive spring 270 from the pre-primed position to a primed position in which the boss 264 on the lancet body 260 abuts the detent 227 on the housing body 220 preventing forward movement of the lancet body 260 in the passage 219. This forward movement of the lancet 250 in the passage 219 also means that the lancet body 260 has moved forwardly past the longitudinal leg 238 such that it can be deflected downwardly in the passage 219. More specifically, both of the lancet wings 266 has moved forwardly past the forwardmost edge of the longitudinal leg 238.

This in turn means that the trigger member 235 can be depressed in an actuation direction transverse to the longitudinal axis of the passage 219 from a rest position to a fire position (i.e. the device is primed and ready to fire). As the lancet wings 266 are positioned in front of the longitudinal leg 238, they do not contact the longitudinal leg 238 when the trigger is depressed and there is no inhibition of transverse movement.

The boss 264 on the lancet body 260 is visible to the user in the window 218. The user can therefore see that the lancet 250 has moved forwardly in the passage 219 from the pre-primed position in which the forward surface of the boss 264 is rearward of the detent 227 to the primed position with the forward surface of the boss 264 abuts the detent 227. Thus, the user can see that the lancet 250 is primed and it is ready to fire.

Neither the cap 290 nor the longitudinal leg 238 are preventing deflection of the lancet body 260 within the passage 219 of the housing body 220. In use, the user will hold the front face 221 of the blood sampling device 201 against the skin, position their thumb or finger on the finger pad 38 and depress the trigger member 235 in an actuation direction A (transverse to the longitudinal axis of the passage 219) from a rest position to a fire position. This is enabled because neither the cap 290 nor the longitudinal leg 238 are longer preventing deflection of the lancet 250. Initial depression of the trigger member 235 flexes it inward into the passage 219 of the housing body 220 such that the lower surface of the trigger member 235 contacts the boss 264 of the lancet body 260. Further depression of the trigger member 235 forces the boss 264 (and therefore the entirety of the forward portion of the lancet body 260) downwards within the passage 219. From this point, the blood sampling device 201 of the second embodiment functions in the same way as the blood sampling device 201 of the first embodiment of the present invention.

Embodiment 3

Figure 20:
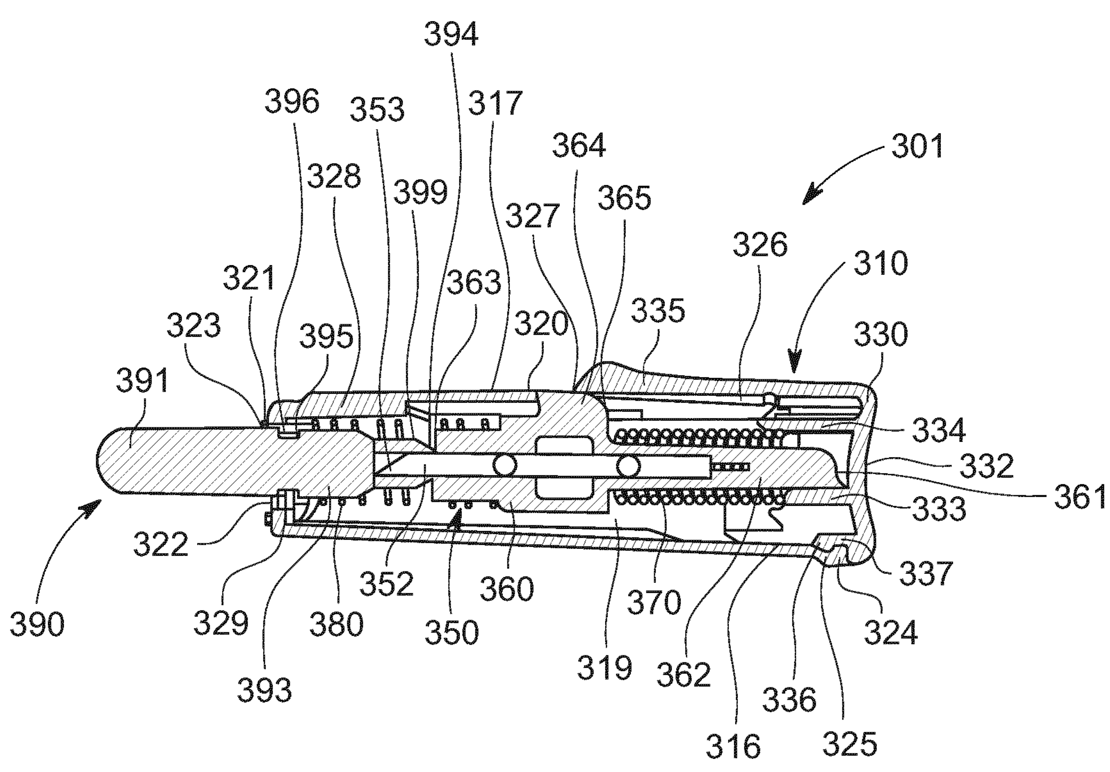
FIG. 20 is a schematic longitudinal cross-sectional side view of a blood sampling device according to a third exemplary embodiment of the present invention in an initial assembled configuration with the lancet in a pre-primed position.
Figure 21:
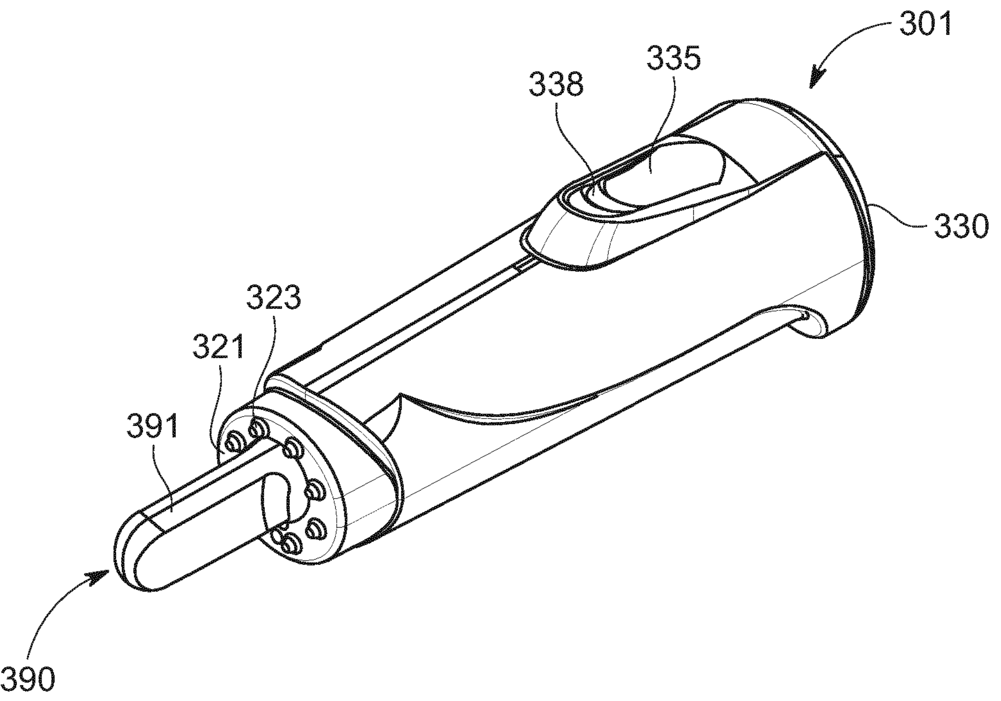
FIG. 21 is a longitudinal cross-sectional side view of the blood sampling device of FIG. 20 with the cap removed and with the lancet in a primed position.

Referring to FIGS. 20 and 21, a blood sampling device 301 according to a third exemplary embodiment of the present invention comprises the same features and works in the same way as the blood sampling device 1 of the first exemplary embodiment. As such, like features will be denoted with like reference numerals but starting from 300.

The blood sampling device 301 of the third embodiment differs from the blood sampling device 1 of the first embodiment in that the trigger member 335 extends to the end of the elongate cut-out 326 in the housing body 320. As such, there is no a gap or window between the forwardmost surface of the trigger member 335 and the forward end of the elongate cut-out 326. Therefore, the user cannot see the boss 364 on the lancet body 360 when the blood sampling device 301 is assembled.

The boss 364 on the lancet body 360 does not rest on a detent provided by the forward end of the elongate cut-out 326 in the housing body 320. Instead, the passage 319 comprises a rearwardly extending rib 317, the rearmost end of which forms a detent 327 against which the boss 364 on the lancet body 360 rests in the initial assembled configuration.

The cap is removed in the same way as in the above embodiments. Once the cap 390 has been removed from the housing body 320, the blood sampling device 301 is primed and the lancet 350 is ready to be fired. The boss 364 on the lancet body 360 abuts the detent 327 on the housing body 320 preventing forward movement of the lancet body 360 in the passage 319. When the trigger member 335 is depressed into the fire position, the forward surface of the boss 264 is moved out of engagement with the detent 327 such that it is no longer abutting the detent 327 (i.e. the forward surface of the boss 364 and the detent 327 are not vertically aligned). From this point, the blood sampling device 301 of the third embodiment functions in the same way as the blood sampling device 201 of the first and second embodiments of the present invention.

Although the third embodiment has been described as separate from the second embodiment it will be understood that any or all of the features described to prevent premature firing of the lancet may be combined.

Figure 22:
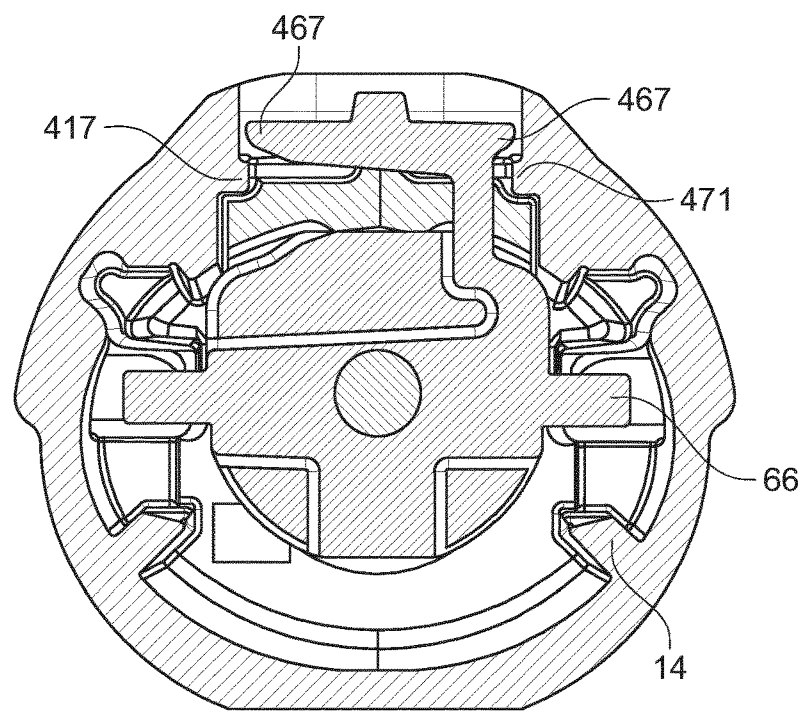
FIG. 22 is a longitudinal cross-section of a blood sampling device in the primed position.
Figure 23:
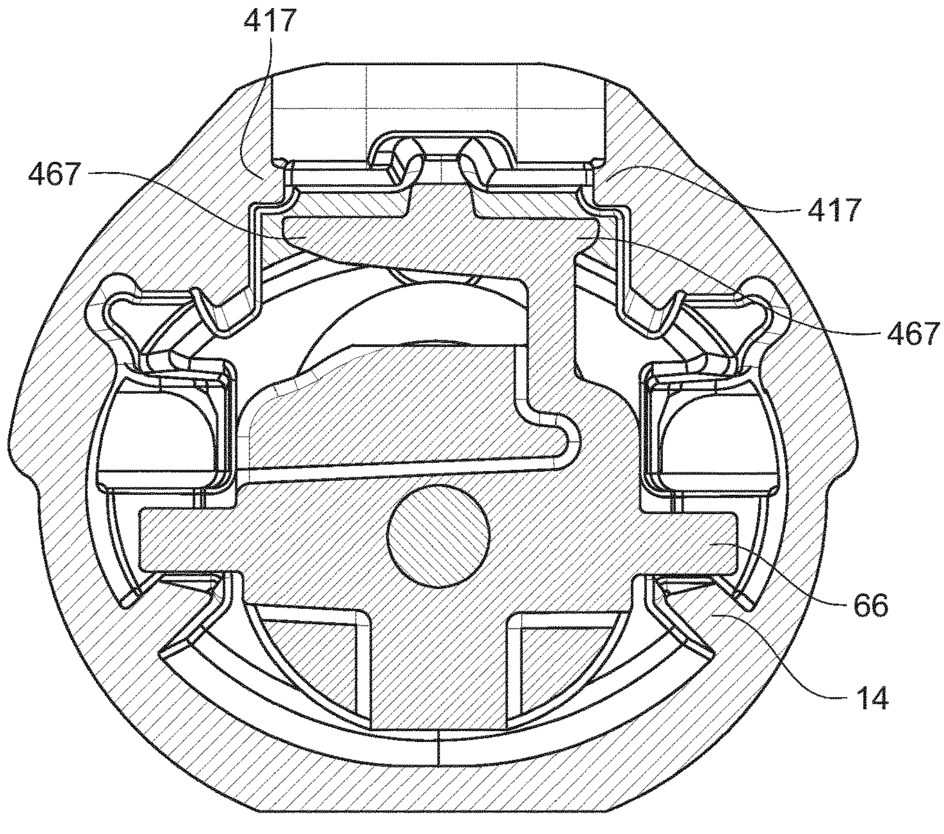
FIG. 23 is a longitudinal cross-section of a blood sampling device after firing.

Another option to prevent premature firing of the lancet which may be combined with any one or more of Embodiments 1 to 3 is shown in FIGS. 22 and 23. In these figures the boss 464 is provided with one or more horizontal projections 467. The horizontal projection 467 can be seen to engage with a lip 417 on the housing surrounding the window. The boss is held above the lip, and thus in engagement with the detent 427 when the trigger is not depressed. When the trigger is depressed the projection contacting the boss can flex sufficiently that the boss 464 is moved out of engagement with the detent 427 thereby allowing firing of the device. By providing the horizontal projections 467 any premature firing of the lancet through deflection of the lancet by the cap 91 may be prevented as the presence of the lip will prevent the boss 464 moving out of engagement with the detent 427 unless the trigger is depressed. Although in FIGS. 22 and 23 the boss 464 comprises a horizontal elongate member connected to the lancet body through an arm it will be understood that any other configuration which allows sufficient flex of the boss will function in this manner.

It will be apparent to a person skilled in the art that modifications and variations can be made to the described embodiment without departing from the scope of the invention as defined by the appended claims. In particular any mechanism described within any embodiment may be combined within other embodiments either singularly or combined. For example, the safety cap may only require a 90° rotation to break the frangible connection between the stem of the safety cap and the lancet body.

The invention claimed is:

1. A blood sampling device comprising:

(i) a housing having an aperture in a forward end thereof and defining a passage having a longitudinal axis;

(ii) a lancet comprising a lancet body supporting a lancet tip at a forward end thereof, said lancet being moveably mounted within said housing;

(iii) an urging member configured to urge said lancet forwardly in said housing in use from a primed position in which said lancet tip is located within said passage to a lancing position in which said lancet tip projects through said aperture in said forward end of said housing;

(iv) a removable safety cap configured to at least partially cover said lancet tip in said passage in an initial assembled configuration;

wherein said housing and said safety cap comprise cooperating abutment surfaces and cooperating stop surfaces, wherein the safety cap is rotatable in a first direction relative to said passage from a first blocked position in which said cooperating abutment surfaces are in abutment alignment to prevent removal of said safety cap from said housing to a second passage position in which said cooperating abutment surfaces are not in abutment alignment such that said safety cap can be removed from said housing; and wherein said stop surfaces cooperate to limit further rotation of said safety cap relative to said passage in said first direction when said safety cap is in said second passage position.

2. A blood sampling device according to claim 1, wherein said housing and said safety cap each comprise second cooperating stop surfaces and wherein the safety cap is rotatable in a second direction relative to said passage from said first blocked position to a third passage position in which said abutment surfaces are not in abutment alignment such that said safety cap can be removed from said housing, wherein the second cooperating stop surfaces cooperate to prevent further rotation of the safety cap relative to said passage in said second direction when said safety cap is in said third passage position.

3. A blood sampling device according to claim 2, wherein movement of said safety cap from said first blocked position to said third passage position requires a predetermined degree of rotational movement in said second direction of between 50° and 70°.

4. A blood sampling device according claim 2, wherein said safety cap is frangibly connected to said lancet body.

5. A blood sampling device according to claim 4, wherein the rotation of said safety cap from the first blocked position to the second passage position is sufficient to sever a frangible connection between the safety cap and the lancet body.

6. A blood sampling device according to claim 4, wherein the rotation of said safety cap from the first blocked position to the second passage position and/or the third passage position is sufficient to sever a frangible connection between the safety cap and the lancet body.

7. A blood sampling device according to claim 4, wherein the stop surfaces are formed by protrusions on said housing and said safety cap.

8. A blood sampling device according claim 7 wherein a stop surface of either the housing and/or the safety cap comprises an angled portion.

9. A blood sampling device according to claim 7 wherein the stop surface of the housing and/or the safety cap comprises a cam surface.

10. A blood sampling device according to claim 2, wherein the abutment surfaces cooperate to prevent forward movement of the safety cap during the rotation of the safety cap from the first blocked position to the second passage position and/or the third passage position.

11. A blood sampling device according to claim 2, wherein the cooperating abutment surfaces are formed by an abutment projection on one of said housing and said safety cap, and a ledge on the other of the housing and said safety cap.

12. A blood sampling device according to claim 11, wherein the cooperating abutment surfaces are formed by the abutment projection on said housing and the ledge on said safety cap.

13. A blood sampling device according to claim 12, wherein the safety cap comprises at least one longitudinal channel radially between the ledge and at least one of the cooperating stop surfaces or the second cooperating stop surfaces through which the abutment projection can pass when said safety cap is in the second passage position such that said safety cap can be removed from said housing.

14. A blood sampling device according to claim 12, wherein the safety cap comprises at least one longitudinal channel radially between the ledge and at least one of the cooperating stop surfaces or the second cooperating stop surfaces through which the abutment projection can pass when said safety cap is in the second passage position or the third passage position such that said safety cap can be removed from said housing.

15. A blood sampling device according to claim 12, wherein the safety cap comprises a protrusion and a forward surface of the protrusion forms the ledge on said safety cap.

16. A blood sampling device according to claim 12, wherein said safety cap defines an arcuate slot therein configured to receive the abutment projection on the housing, a rearward surface of the slot forming the ledge on said safety cap.

17. A blood sampling device according to claim 16, wherein the abutment projection on the housing forms at least one of the cooperating stop surfaces or the second cooperating stop surfaces and at least one stop projection is provided in the arcuate slot of said safety cap to form another one of the at least one of the cooperating stop surfaces or the second cooperating stop surfaces.

18. A blood sampling device according to claim 1, wherein movement of said safety cap from said first blocked position to said second passage position requires a predetermined degree of rotational movement in said first direction of between 50° and 70°.

19. A blood sampling device according to claim 1, wherein the abutment surfaces cooperate to prevent forward movement of the safety cap during the rotation of the safety cap from the first blocked position to the second passage position.

20. A blood sampling device according to claim 1, wherein at least one of said safety cap and said lancet body comprises an anti-deflection feature configured to interact with the other of said lancet body and said safety cap to restrict a degree to which said safety cap and said lancet body can be misaligned relative to the longitudinal axis in the initial assembled configuration.

21. A blood sampling device according to claim 20, wherein said safety cap and said lancet body comprise adjacent surfaces frangibly connected by a narrowing therebetween and said anti-deflection feature is a protrusion on at least one of said adjacent surfaces configured to interact with the other of said adjacent surfaces.

22. A blood sampling device according to claim 1, further comprising means for preventing rearward movement of said lancet body from said lancing position to said primed position.

* * * * *